(12) United States Patent
Morinaka et al.

(10) Patent No.: US 10,507,251 B2
(45) Date of Patent: *Dec. 17, 2019

(54) ANTI-HUMAN MUC1 ANTIBODY FAB FRAGMENT

(71) Applicant: Astellas Pharma Inc., Tokyo (JP)

(72) Inventors: Akifumi Morinaka, Tokyo (JP); Hiroki Shirai, Tokyo (JP); Kazunori Hirayama, Tokyo (JP); Naomi Hosogai, Tokyo (JP); Hitoshi Doihara, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/414,895

(22) Filed: May 17, 2019

(65) Prior Publication Data

US 2019/0269804 A1 Sep. 5, 2019

Related U.S. Application Data

(63) Continuation-in-part of application No. PCT/JP2017/041486, filed on Nov. 17, 2017.

(30) Foreign Application Priority Data

Nov. 18, 2016 (JP) .................... 2016-224811

(51) Int. Cl.
*A61K 49/00* (2006.01)
*A61K 47/68* (2017.01)
(Continued)

(52) U.S. Cl.
CPC ...... *A61K 49/0058* (2013.01); *A61K 47/6855* (2017.08); *A61K 49/0032* (2013.01);
(Continued)

(58) Field of Classification Search
None
See application file for complete search history.

(56) References Cited

U.S. PATENT DOCUMENTS

2012/0040375 A1 2/2012 Nishimura et al.
2013/0045543 A1 2/2013 Nishimura et al.

FOREIGN PATENT DOCUMENTS

JP 2010-505775 A 2/2010
WO 2008/040362 A2 4/2008
(Continued)

OTHER PUBLICATIONS

U.S. Appl. No. 16/462,143, filed May 17, 2019, Morinaka, Akifumi et al.

(Continued)

*Primary Examiner* — Karl J Puttlitz
(74) *Attorney, Agent, or Firm* — Oblon, McClelland, Maier & Neustadt, L.L.P.

(57) ABSTRACT

The problem to be solved is to provide an anti-human MUC1 antibody Fab fragment that is expected to be useful in the diagnosis and/or treatment of a cancer, particularly, the diagnosis and/or treatment of breast cancer or bladder cancer, and a diagnosis approach and/or a treatment approach using a conjugate comprising the Fab fragment. The solution is an anti-human MUC1 antibody Fab fragment comprising a heavy chain fragment comprising a heavy chain variable region consisting of the amino acid sequence represented by SEQ ID NO: 8 or 10, and a light chain comprising a light chain variable region consisting of the amino acid sequence represented by SEQ ID NO: 12, and a conjugate comprising the Fab fragment.

17 Claims, 6 Drawing Sheets

Specification includes a Sequence Listing.

(51) Int. Cl.
*C07K 16/30* (2006.01)
*A61P 35/00* (2006.01)

(52) U.S. Cl.
CPC .......... *A61K 49/0036* (2013.01); *A61P 35/00* (2018.01); *C07K 16/3092* (2013.01); *C07K 2317/55* (2013.01); *C07K 2317/76* (2013.01); *C07K 2317/92* (2013.01)

(56) References Cited

FOREIGN PATENT DOCUMENTS

| WO | 2010/050528 A1 | 5/2010 |
| WO | 2011/135869 A1 | 11/2011 |
| WO | 2016/130726 A1 | 8/2016 |

OTHER PUBLICATIONS

International Search Report dated Feb. 13, 2018 issued in corresponding application PCT/JP2017/041486 (citing documents AO-AR therein).

Kirstine Lavrsen et al; Aberrantly glycosylated MUC1 is expressed on the surface of breast cancer cells and a target for antibody-dependent cell-mediated cytotoxicity; Glycoconj. J., Apr. 2013; 30 (3): pp. 227-236.

Antje Danielczyk et al; PankoMab: a potent new generation antitumor MUC1 antibody; Cancer Immunol Immunother. Nov. 2006; 55 (11): pp. 1337-1347.

| ANTIBODY NAME | P10-2 Fab | P10-2 Fab DFO |
|---|---|---|
| Kd (nM) | 0.37 | 0.36 |
| <95% CI> | <0.07-2.06> | <0.05-2.36> |

ANTI-HUMAN MUC1 ANTIBODY FAB FRAGMENT

This application is a continuation-in-part of international application No. PCT/JP2017/041486, filed on Nov. 17, 2017.

TECHNICAL FIELD

The present invention relates to a novel anti-human MUC1 antibody Fab fragment. The present invention also relates to a composition for diagnosis and/or for treatment comprising the anti-human MUC1 antibody Fab fragment, and a method for diagnosing and/or treating a cancer using the Fab fragment.

BACKGROUND ART

Mucin 1 (MUC1) is a membrane-bound glycoprotein that is expressed on the lumen side of epithelial cells constituting the epithelial tissues of the mammary gland, the trachea and the gastrointestinal tract, etc. (Nat. Rev. Cancer, 2004 January; 4 (1): 45-60). MUC1 is overexpressed in cancer cells of breast cancer (Mod. Pathol., 2005 October; 18 (10): 1295-304), lung cancer (Hum. Pathol., 2008 January; 39 (1): 126-36), colorectal cancer (Int. J. Oncol., 2000 January; 16 (1): 55-64), bladder cancer (PLoS One, 2014 March; 9 (3): e92742), skin cancer (Histopathology, 2000 September; 37 (3): 218-23), thyroid gland cancer (J. Pathol., 2003 July; 200 (3): 357-69), stomach cancer (J. Pathol., 2000 March; 190 (4): 437-43), pancreatic cancer (Int. J. Oncol., 2004 January; 24 (1): 107-13), kidney cancer (Mod. Pathol., 2004 February; 17 (2): 180-8), ovary cancer (Gynecol. Oncol., 2007 June; 105 (3): 695-702) and uterine cervical cancer (Am. J. Clin. Pathol., 2004 July; 122 (1): 61-9), etc. MUC1 is useful as a target molecule for detecting a cancer focus (Nat. Rev. Cancer, 2004 January; 4 (1): 45-60; and Pathol. Res. Pract., 2010 Aug. 15; 206 (8): 585-9).

MUC1 undergoes the O-glycosylation of threonine at position 9 of a 20-amino acid tandem repeat sequence HGVTSAPDTRPAPGSTAPPA (SEQ ID NO: 15) present in an extracellular domain. In cancer cells, this O-glycosylation is incomplete, and O-glycosylation such as T(Galβ1-3GalNAcα1-O-Ser/Thr), Tn(GalNAcα1-O-Ser/Thr) and 2,3ST(Neu5Acα2-3Galβ1-3GalNAcα-O-Ser/Thr) is known to occur in a cancer-specific manner (PTL 1 and NPL 1). Since MUC1 in normal tissues does not undergo such cancer-specific O-glycosylation, human cancer-specific MUC1 is particularly useful as a target molecule for treating various cancers in humans.

For example, a 1B2 antibody (PTL 1), a PankoMab antibody (NPL 2), and a 5E5 antibody (PTL 2) are known as antibodies against such human cancer-specific MUC1. Among these antibodies, the 1B2 antibody has been reported to have high specificity for human cancer-specific MUC1 as compared with the PankoMab antibody (PTL 1). It has also been reported that the dissociation constant of the 1B2 antibody is $3.7 \times 10^{-10}$ M (PTL 1), and the dissociation constant of the 5E5 antibody is $1.7 \times 10^{-9}$ M (NPL 1).

Meanwhile, there are also great needs for the visualization of cancer lesion. First, there are the needs for the early detection of cancer lesion. Current diagnostic modalities such as X-ray photography, echography, computed tomography (CT), magnetic resonance imaging (MRI), positron emission tomography (PET), and single photon emission computed tomography (SPECT) cannot sensitively detect micro cancers. If micro cancers can be detected, a primary cancer can be cured by operation or radiotherapy or even a metastatic cancer is curable for a life-sustaining way by early pharmaceutical intervention. Next, there are the needs for the differentiation between a cancer lesion and a benign lesion. The current diagnostic modalities often misdiagnose a benign lesion as a cancer lesion. If differentiation can be made between a cancer lesion and a benign lesion, unnecessary biopsy can be decreased. Furthermore, there are the needs for the intraoperative visualization of cancer lesion. At present, the position or extent of a cancer lesion cannot be accurately determined during the operation of cancers including breast cancer, bladder cancer, and skin cancer. Therefore, the cancer lesion cannot be completely resected, and there is a risk of ending the operation while leaving the cancer cells. Moreover, there are the needs for the correct determination of the positions of cancer lesion. Even if postoperative recurrence and metastasis are suspected due to the elevation of a tumor marker in blood, the current diagnostic modalities cannot visualize a metastatic micro cancer. Therefore, the optimum treatment cannot be selected because whether or not the cancer has actually metastasized or which organ the cancer has metastasized to cannot be determined. Thus, it is also useful to visualize cancer lesion by molecular imaging techniques such as fluorescent imaging and γ-ray imaging (PET and SPECT) using an antibody specifically binding to human cancer-specific MUC1 as an in vivo diagnostic drug. However, any previous case using an anti-human cancer-specific MUC1 antibody as an in vivo diagnostic drug has not been known.

There is the further needs for a cancer therapeutic drug such as drug conjugated an antibody. The antibody drug is expected as a method for treating a cancer with fewer adverse reactions because of specific delivery to a cancer lesion. Radioimmunotherapy using an antibody bound to a radioisotope (Takashi Tsuruo, "Molecular Target Therapy of Cancer", NANZANDO Co., Ltd., published on Sep. 15, 2008, p. 332-336; J. Nucl. Med., 2016 July; 57 (7): 1105-1111; and Nucl. Med. Biol., 2010 November; 37 (8): 949-955), photoimmunotherapy using an antibody bound to IRDye700DX (Nat. Med., 2011 December; 17 (12): 1685-91), and the like have been reported. IRDye700DX is a near-infrared fluorescent dye that can also be used in diagnosis. It has been reported that cell death can be induced in a cancer-specific manner through the phototoxic effect of IRDye700DX by binding this to an antibody against an antigen expressed on a cancer cell membrane, and allowing the resultant to specifically accumulate in cancer tissues, followed by irradiation with near-infrared light (Nat. Med., 2011 December; 17 (12): 1685-91). However, any previous case of clinically applying an antibody drug of an anti-human cancer-specific MUC1 antibody bound to a cancer therapeutic drug has not been known.

In general, antibodies have a long half-life in blood and require a period as long as 4 days to 5 days for reaching a tumor-to-blood ratio that confers a signal-to-background ratio sufficient for visualizing a cancer, after administration into the body (Clin. Pharmacol. Ther., 2010 May; 87 (5): 586-92). Also, the Fc regions of antibodies cause a pharmacological effect such as antibody-dependent cellular cytotoxicity (ADCC) or complement-dependent cytotoxicity (CDC) (NPL 1; and Curr. Opin. Biotechnol., 2002 December; 13 (6): 609-14). Furthermore, antibodies highly accumulate in the liver regardless of a target, and cancer cells such as breast cancer are highly to metastasize to the liver. The accumulation in the liver interfere with the detection of hepatic metastasis at the time of diagnosis of systemic cancer lesion (Clin. Pharmacol. Ther., 2010 May; 87 (5): 586-92).

For example, low-molecular recombinant antibody fragments such as Fab, scFv, diabody, and minibody are expected to be utilized as therapeutic antibodies because of easy reaching to foci with their high tissue penetration and low cost production by using an expression system in *E. coli* or yeast. And also, they are reported to be utilized as diagnostic drug because of their short half-lives in blood and the feature of renal excretion (Nat. Biotechnol., 2005 September; 23 (9): 1126-36).

CITATION LIST

Patent Literature

PTL 1: WO2010/050528
PTL 2: WO2008/040362

Non Patent Literature

NPL 1: Glycoconj. J., 2013 April; 30 (3): 227-36
NPL 2: Cancer Immunol Immunother, 2006 November; 55 (11): 1337-47

SUMMARY OF INVENTION

Technical Problem

Monovalent Fab fragments have a molecular weight of approximately 50 kDa, which is smaller than antibodies which have a molecular weight of approximately 150 kDa, are eliminated by renal excretion, and also have a short half-life in blood. Hence, they reach a tumor-to-blood ratio that confers a signal-to-background ratio sufficient for visualizing a cancer, within 2 to 32 hours after administration. They lack an Fc region and therefore cause neither ADCC nor CDC. The Fab fragments are typically eliminated by renal excretion and therefore, do not interfere with the detection of hepatic metastasis. From these features, the Fab fragments can be expected to be more effective as in vivo diagnostic drugs as compared with antibodies.

However, the binding activity of the Fab fragments is often attenuated because of being monovalent, not divalent. Antibodies must be labeled with a detectable substance such as a fluorescent dye or a contrast medium for their utilization as in vivo diagnostic drugs or drugs for use in photoimmunotherapy methods. A further problem is the attenuation of their binding activity due to labeling with such a substance.

An object of the present invention is to provide an anti-human MUC1 antibody Fab fragment that has excellent binding activity and is expected to accumulate in a cancer focus within a given time (e.g., 24 hours) after administration. Another object of the present invention is to provide a composition for diagnosis comprising the Fab fragment and a diagnosis method using the same, and to provide a composition for treatment comprising the Fab fragment and a treatment method using the same.

Solution to Problem

The present inventors have conducted considerable diligent studies on the preparation of an anti-human MUC1 antibody Fab fragment having excellent binding activity against human cancer-specific MUC1, and consequently prepared an anti-human MUC1 antibody Fab fragment comprising a heavy chain variable region consisting of the amino acid sequence represented by SEQ ID NO: 8 or SEQ ID NO: 10, and a light chain variable region consisting of the amino acid sequence represented by SEQ ID NO: 12 (Example 1) and found that: the anti-human MUC1 antibody Fab fragment has excellent binding activity against human cancer-specific MUC1 (Example 3) and is free from the attenuation of the binding activity against human cancer-specific MUC1 by fluorescent labeling and labeling with a chelating agent (Example 5 and Example 7); and a conjugate comprising the anti-human MUC1 antibody Fab fragment is useful in the diagnosis of cancers (Example 8, Example 12 and Example 13) and exhibits an antitumor effect in subcutaneously cancer-bearing models (Example 15).

As a result, a diagnosis approach and a treatment approach using the anti-human MUC1 antibody Fab fragment and the conjugate comprising the anti-human MUC1 antibody Fab fragment are provided.

The present invention includes aspects given below as medically or industrially useful substances and methods.

Specifically, in one aspect, the present invention can be as follows:

[1] An anti-human MUC1 antibody Fab fragment selected from the group consisting of the following (a) and (b):
(a) an anti-human MUC1 antibody Fab fragment comprising a heavy chain fragment comprising a heavy chain variable region consisting of the amino acid sequence represented by SEQ ID NO: 8 or SEQ ID NO: 10 and a light chain comprising a light chain variable region consisting of the amino acid sequence represented by SEQ ID NO: 12; and
(b) an anti-human MUC1 antibody Fab fragment comprising a heavy chain fragment comprising a heavy chain variable region derived from a heavy chain variable region consisting of the amino acid sequence represented by SEQ ID NO: 8 or SEQ ID NO: 10 by the modification of glutamine at amino acid position 1 of SEQ ID NO: 8 or SEQ ID NO: 10 into pyroglutamic acid, and a light chain comprising a light chain variable region consisting of the amino acid sequence represented by SEQ ID NO: 12.

[2] The anti-human MUC1 antibody Fab fragment according to [1] which is selected from the group consisting of the following (a) and (b):
(a) an anti-human MUC1 antibody Fab fragment comprising a heavy chain fragment consisting of the amino acid sequence represented by SEQ ID NO: 2 or SEQ ID NO: 4 and a light chain consisting of the amino acid sequence represented by SEQ ID NO: 6; and
(b) an anti-human MUC1 antibody Fab fragment comprising a heavy chain fragment derived from a heavy chain fragment consisting of the amino acid sequence represented by SEQ ID NO: 2 or SEQ ID NO: 4 by the modification of glutamine at amino acid position 1 of SEQ ID NO: 2 or SEQ ID NO: 4 into pyroglutamic acid, and a light chain consisting of the amino acid sequence represented by SEQ ID NO: 6.

[3] The anti-human MUC1 antibody Fab fragment according to [1] which is selected from the group consisting of the following (a) and (b):
(a) an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12; and
(b) an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12.

[4] The anti-human MUC1 antibody Fab fragment according to [3] which is selected from the group consisting of the following (a) and (b):
(a) an anti-human MUC1 antibody Fab fragment comprising a heavy chain fragment consisting of the amino acid sequence represented by SEQ ID NO: 4 and a light chain consisting of the amino acid sequence represented by SEQ ID NO: 6; and
(b) an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

[5] The anti-human MUC1 antibody Fab fragment according to [4] which is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6.

[6] The anti-human MUC1 antibody Fab fragment according to [4] which is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

[7] A conjugate comprising one or more labeling moiety and the anti-human MUC1 antibody Fab fragment according to any of [1] to [6].

[8] The conjugate according to [7], wherein the labeling moiety is (i) a ligand and a linker, (ii) a ligand, (iii) a fluorescent dye and a linker, or (iv) a fluorescent dye.

[9] The conjugate according to [8], wherein the labeling moiety is (i) a ligand and a linker or (ii) a ligand.

[10] The conjugate according to [9], wherein the ligand is a ligand represented by the following formula (A):

[Formula 1]

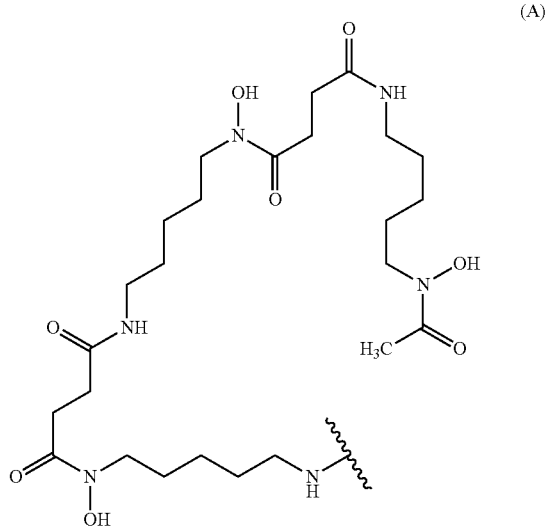

(A)

wherein the wavy line represents binding to the anti-human MUC1 antibody Fab fragment or the linker.

[11] The conjugate according to [10], wherein the labeling moiety is a ligand and a linker represented by the following formula (A'):

[Formula 2]

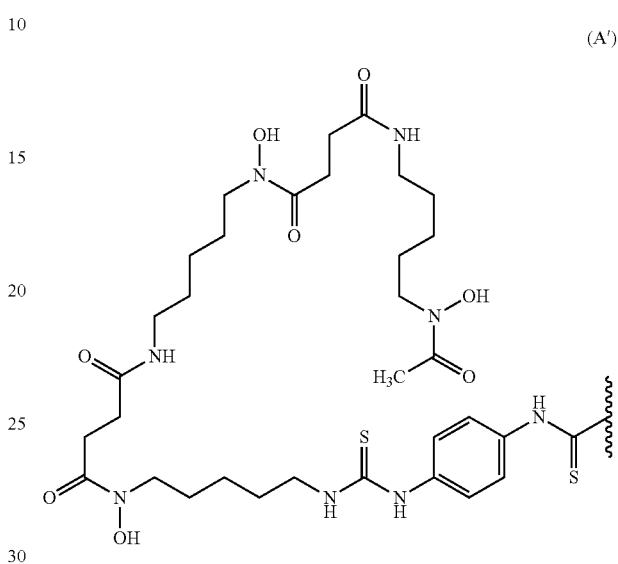

(A')

wherein the wavy line represents binding to the anti-human MUC1 antibody Fab fragment.

[12] The conjugate according to [11], wherein the anti-human MUC1 antibody Fab fragment is bound via an amino group thereof to the carbon atom of a labeling moiety terminal C(=S) group.

[13] A conjugate selected from the group consisting of the following (a) to (c):
(a) the conjugate according to [12] wherein the anti-human MUC1 antibody Fab fragment is the anti-human MUC1 antibody Fab fragment according to [5];
(b) the conjugate according to [12] wherein the anti-human MUC1 antibody Fab fragment is the anti-human MUC1 antibody Fab fragment according to [6]; and
(c) a conjugate which is a mixture of (a) and (b).

[14] The conjugate according to any of [9] to [13], further comprising a metal.

[15] The conjugate according to [14], wherein the metal is a metal radioisotope.

[16] The conjugate according to [15], wherein the metal is $^{89}$Zr.

[17] The conjugate according to [13], further comprising $^{89}$Zr.

[18] The conjugate according to [8], wherein the labeling moiety is (i) a fluorescent dye and a linker or (ii) a fluorescent dye.

[19] The conjugate according to [18], wherein the fluorescent dye is a fluorescent dye selected from the group consisting of the following formula (B) and the following formula (C):

[Formula 3]

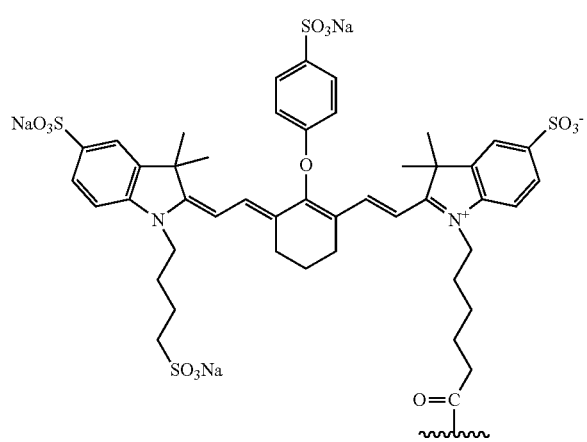

[Formula 4]

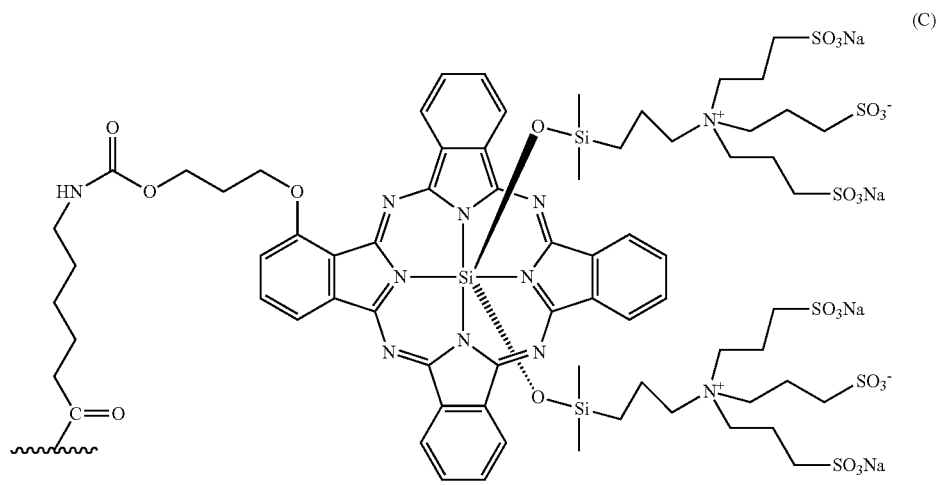

wherein the wavy line represents binding to the anti-human MUC1 antibody Fab fragment or the linker.

[20] The conjugate according to [19], wherein the wavy line represents binding to the anti-human MUC1 antibody Fab fragment, and the anti-human MUC1 antibody Fab fragment is bound via an amino group thereof to the carbon atom of a labeling moiety terminal C(=O) group.

[21] The conjugate according to [20], wherein the labeling moiety is a fluorescent dye represented by formula (B).

[22] A conjugate selected from the group consisting of the following (a) to (c):
(a) the conjugate according to [21] wherein the anti-human MUC1 antibody Fab fragment is the anti-human MUC1 antibody Fab fragment according to [5];
(b) the conjugate according to [21] wherein the anti-human MUC antibody Fab fragment is the anti-human MUC1 antibody Fab fragment according to [6]; and
(c) a conjugate which is a mixture of (a) and (b).

The conjugate according to [20], wherein the labeling moiety is a fluorescent dye represented by formula (C).

[23] A conjugate selected from the group consisting of the following (a) to (c):
(a) the conjugate according to [23] wherein the anti-human MUC1 antibody Fab fragment is the anti-human MUC1 antibody Fab fragment according to [5];
(b) the conjugate according to [23] wherein the anti-human MUC1 antibody Fab fragment is the anti-human MUC1 antibody Fab fragment according to [6]; and
(c) a conjugate which is a mixture of (a) and (b).

[25] A polynucleotide selected from the group consisting of the following (a) and (b):
(a) a polynucleotide comprising a nucleotide sequence encoding the heavy chain fragment of the anti-human MUC1 antibody Fab fragment according to [1]; and
(b) a polynucleotide comprising a nucleotide sequence encoding the light chain of the anti-human MUC1 antibody Fab fragment according to [1].

[26] A polynucleotide selected from the group consisting of the following (a) and (b):
(a) a polynucleotide comprising a nucleotide sequence encoding the heavy chain fragment of the anti-human MUC1 antibody Fab fragment according to [5]; and
(b) a polynucleotide comprising a nucleotide sequence encoding the light chain of the anti-human MUC1 antibody Fab fragment according to [5].

[27] An expression vector comprising the following (a) and/or (b):
(a) a polynucleotide comprising a nucleotide sequence encoding the heavy chain fragment of the anti-human MUC1 antibody Fab fragment according to [1]; and
(b) a polynucleotide comprising a nucleotide sequence encoding the light chain of the anti-human MUC1 antibody Fab fragment according to [1].

[28] An expression vector comprising the following (a) and/or (b):
(a) a polynucleotide comprising a nucleotide sequence encoding the heavy chain fragment of the anti-human MUC1 antibody Fab fragment according to [5]; and
(b) a polynucleotide comprising a nucleotide sequence encoding the light chain of the anti-human MUC1 antibody Fab fragment according to [5].

[29] A host cell selected from the group consisting of the following (a) to (d):
(a) a host cell transformed with an expression vector comprising a polynucleotide comprising a nucleotide sequence encoding the heavy chain fragment of the anti-human MUC1 antibody Fab fragment according to [1];

(b) a host cell transformed with an expression vector comprising a polynucleotide comprising a nucleotide sequence encoding the light chain of the anti-human MUC1 antibody Fab fragment according to [1];
(c) a host cell transformed with an expression vector comprising a polynucleotide comprising a nucleotide sequence encoding the heavy chain fragment of the anti-human MUC1 antibody Fab fragment according to [1] and a polynucleotide comprising a nucleotide sequence encoding the light chain of the anti-human MUC1 antibody Fab fragment according to [1]; and
(d) a host cell transformed with an expression vector comprising a polynucleotide comprising a nucleotide sequence encoding the heavy chain fragment of the anti-human MUC1 antibody Fab fragment according to [1] and an expression vector comprising a polynucleotide comprising a nucleotide sequence encoding the light chain of the anti-human MUC1 antibody Fab fragment according to [1].
[30] A host cell selected from the group consisting of the following (a) to (d):
(a) a host cell transformed with an expression vector comprising a polynucleotide comprising a nucleotide sequence encoding the heavy chain fragment of the anti-human MUC1 antibody Fab fragment according to [5];
(b) a host cell transformed with an expression vector comprising a polynucleotide comprising a nucleotide sequence encoding the light chain of the anti-human MUC1 antibody Fab fragment according to [5];
(c) a host cell transformed with an expression vector comprising a polynucleotide comprising a nucleotide sequence encoding the heavy chain fragment of the anti-human MUC1 antibody Fab fragment according to [5] and a polynucleotide comprising a nucleotide sequence encoding the light chain of the anti-human MUC1 antibody Fab fragment according to [5]; and
(d) a host cell transformed with an expression vector comprising a polynucleotide comprising a nucleotide sequence encoding the heavy chain fragment of the anti-human MUC1 antibody Fab fragment according to [5] and an expression vector comprising a polynucleotide comprising a nucleotide sequence encoding the light chain of the anti-human MUC1 antibody Fab fragment according to [5].
[31] A method for producing an anti-human MUC1 antibody Fab fragment comprising the step of culturing a host cell selected from the group consisting of the following (a) to (c) to express the anti-human MUC1 antibody Fab fragment:
(a) a host cell transformed with an expression vector comprising a polynucleotide comprising a nucleotide sequence encoding the heavy chain fragment of the anti-human MUC1 antibody Fab fragment according to [1] and a polynucleotide comprising a nucleotide sequence encoding the light chain of the anti-human MUC1 antibody Fab fragment according to [1];
(b) a host cell transformed with an expression vector comprising a polynucleotide comprising a nucleotide sequence encoding the heavy chain fragment of the anti-human MUC1 antibody Fab fragment according to [1] and an expression vector comprising a polynucleotide comprising a nucleotide sequence encoding the light chain of the anti-human MUC1 antibody Fab fragment according to [1]; and
(c) a host cell transformed with an expression vector comprising a polynucleotide comprising a nucleotide sequence encoding the heavy chain fragment of the anti-human MUC1 antibody Fab fragment according to [1], and a host cell transformed with an expression vector comprising a polynucleotide comprising a nucleotide sequence encoding the light chain of the anti-human MUC1 antibody Fab fragment according to [1].
[32] A method for producing an anti-human MUC1 antibody Fab fragment comprising the step of culturing a host cell selected from the group consisting of the following (a) to (c) to express the anti-human MUC1 antibody Fab fragment:
(a) a host cell transformed with an expression vector comprising a polynucleotide comprising a nucleotide sequence encoding the heavy chain fragment of the anti-human MUC1 antibody Fab fragment according to [5] and a polynucleotide comprising a nucleotide sequence encoding the light chain of the anti-human MUC1 antibody Fab fragment according to [5];
(b) a host cell transformed with an expression vector comprising a polynucleotide comprising a nucleotide sequence encoding the heavy chain fragment of the anti-human MUC1 antibody Fab fragment according to [5] and an expression vector comprising a polynucleotide comprising a nucleotide sequence encoding the light chain of the anti-human MUC1 antibody Fab fragment according to [5]; and
(c) a host cell transformed with an expression vector comprising a polynucleotide comprising a nucleotide sequence encoding the heavy chain fragment of the anti-human MUC1 antibody Fab fragment according to [5], and a host cell transformed with an expression vector comprising a polynucleotide comprising a nucleotide sequence encoding the light chain of the anti-human MUC1 antibody Fab fragment according to [5].
[33] A method for producing a conjugate comprising a labeling moiety and an anti-human MUC1 antibody Fab fragment, comprising the steps of: producing the anti-human MUC1 antibody Fab fragment by the method according to [31] or [32]; and covalently binding the Fab fragment to the labeling moiety.
[34] The method for producing a conjugate according to [33], wherein the step of covalently binding the Fab fragment to the labeling moiety is the step of i) binding the Fab fragment via a linker to a ligand or ii) covalently binding the Fab fragment directly to a ligand.
[35] The method for producing a conjugate according to [34], further comprising the step of labeling the ligand of the conjugate with a metal radioisotope.
[36] The method for producing a conjugate according to [33], wherein the step of covalently binding the Fab fragment to the labeling moiety is the step of i) binding the Fab fragment via a linker to a fluorescent dye or ii) covalently binding the Fab fragment directly to a fluorescent dye.
[37] A composition for diagnosis comprising one or more conjugate according to any of [7] to [24], and a pharmaceutically acceptable carrier.
[38] The composition for diagnosis according to [37], wherein the conjugate is the conjugate according to any of [17], [22] and [24].
[39] The composition for diagnosis according to [38], wherein the conjugate is the conjugate according to [17].
[40] The composition for diagnosis according to [38], wherein the conjugate is the conjugate according to [22].
[41] The composition for diagnosis according to [38], wherein the conjugate is the conjugate according to [24].
[42] The composition for diagnosis according to any of [37] to [41] which is used in the diagnosis of a cancer expressing human MUC1.
[43] The composition for diagnosis according to [42], wherein the cancer is breast cancer or bladder cancer.

[44] A pharmaceutical composition comprising one or more conjugate according to any of [7] to [24], and a pharmaceutically acceptable carrier.
[45] The pharmaceutical composition according to [44], wherein the conjugate is the conjugate according to any of [17], [22] and [24].
[46] The pharmaceutical composition according to [45], wherein the conjugate is the conjugate according to [24].
[47] The pharmaceutical composition according to any of [44] to [46] which is a pharmaceutical composition for treating a cancer expressing human MUC1.
[48] The pharmaceutical composition according to [47], wherein the cancer is breast cancer or bladder cancer.
[49] Use of the conjugate according to any of [7] to [24] for the production of a composition for the diagnosis of breast cancer or bladder cancer and/or a pharmaceutical composition for treating breast cancer or bladder cancer.
[50] The conjugate according to any of [7] to [24] for use in the diagnosis and/or treatment of breast cancer or bladder cancer.
[51] A method for diagnosing breast cancer or bladder cancer, comprising preoperatively or intraoperatively administering the conjugate according to any of [7] to [24] to a subject.
[52] A method for treating breast cancer or bladder cancer, comprising the step of administering a therapeutically effective amount of the conjugate according to any of [7] to [24].

Advantageous Effects of Invention

The anti-human MUC1 antibody Fab fragment of the present invention has excellent binding activity against human cancer-specific MUC1 and is expected to be useful in the diagnosis and/or treatment of cancers such as breast cancer.

DESCRIPTION OF EMBODIMENTS

Figure 1:
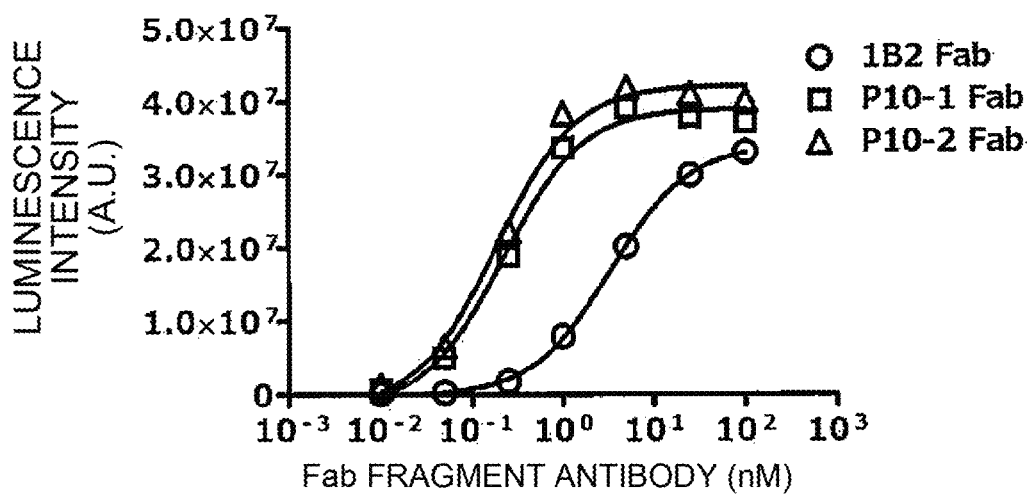
FIG. 1 is a graph and a table showing the binding activity of P10-1 Fab, P10-2 Fab and 1B2 Fab of Comparative Example against human cancer-specific MUC1.

Hereinafter, the present invention will be described in detail. However, the present invention is not limited thereby. Scientific terms and technical terms used in relation to the present invention have meanings generally understood by those skilled in the art, unless otherwise specified herein.

The present inventors have conducted considerable diligent studies on the preparation of an anti-human cancer-specific MUC1 antibody or an antigen binding fragment thereof and consequently successfully prepared an anti-human MUC1 antibody Fab fragment having the ability to strongly bind to cancer-specific MUC1.

The basic structure of an antibody molecule is common among classes and is constituted by heavy chains having a molecular weight of 50000 to 70000 and light chains having a molecular weight of 20000 to 30000. The heavy chain usually consists of a polypeptide chain comprising approximately 440 amino acids, has a structure characteristic of each class, and is called γ, μ, α, δ, and ε chains corresponding to IgG, IgM, IgA, IgD, and IgE. IgG further has IgG1, IgG2, IgG3, and IgG4 which are called γ1, γ2, γ3, and γ4, respectively. The light chain usually consists of a polypeptide chain comprising approximately 220 amino acids and known as two types, L and K types, which are called λ and Ks chains, respectively. As for the peptide configuration of the basic structure of the antibody molecule, two homologous heavy chains and two homologous light chains are linked through disulfide bonds (S—S bonds) and non-covalent bonds to form a molecular weight of 150000 to 190000. The two light chains can pair with any of the heavy chains. An individual antibody molecule is constantly made up of two identical light chains and two identical heavy chains.

Four (or five for μ and ε chains) and two intrachain S—S bonds are present in the heavy chain and the light chain, respectively, and each constitute one loop per 100 to 110 amino acid residues. This conformation is similar among the loops and is called structural unit or domain. For both the heavy chain and the light chain, a domain positioned at the N terminus does not have a constant amino acid sequence even among preparations from the same classes (subclasses) of animals of the same species, and is thus called variable region. The respective domains are called heavy chain variable region (VH domain) and light chain variable region (VL domain). An amino acid sequence on the C-terminal side therefrom is almost constant on a class or subclass basis and called constant region. The respective domains are represented by CH1, CH2, CH3 and CL.

The binding specificity of the antibody for an antigen depends on the amino acid sequence of a moiety constituted by the heavy chain variable region and the light chain variable region. On the other hand, biological activity such as binding to complements or various cells reflects the difference in structure among the constant regions of Igs of respective classes. It is known that the variability of the heavy chain and light chain variable regions is limited substantially by three small hypervariable regions present in both the chains. These regions are called complementarity determining regions (CDRs; CDR1, CDR2, and CDR3 in order from the N-terminal side). The remaining moieties of the variable region are called framework regions (FRs) and are relatively constant.

A region between the CH1 domain and the CH2 domain of the heavy chain constant region of an antibody is called hinge region. This region is rich in proline residues and contains a plurality of interchain S—S bonds that connect two heavy chains. For example, the hinge regions of human IgG1, IgG2, IgG3, and IgG4 contain 2, 4, 11, and 2 cysteine residues, respectively, which constitute S—S bonds between the heavy chains. The hinge region is a region highly sensitive to a proteolytic enzyme such as papain or pepsin. In the case of digesting an antibody with papain, the heavy chains are cleaved at a position on the N-terminal side from the inter-heavy chain S—S bonds of the hinge region and thus decomposed into two Fab fragments and one Fc fragment. The Fab fragment is constituted by a light chain and a heavy chain fragment comprising a heavy chain variable region (VH), a CH1 domain and a portion of the hinge region. The Fab fragment comprises variable regions and has antigen binding activity.

<Anti-Human MUC1 Antibody Fab Fragment of Present Invention>

The anti-human MUC1 antibody Fab fragment of the present invention is a Fab fragment having the following feature:

an anti-human MUC1 antibody Fab fragment comprising a heavy chain fragment comprising a heavy chain variable region consisting of the amino acid sequence represented by SEQ ID NO: 8 or SEQ ID NO: 10 and a light chain comprising a light chain variable region consisting of the amino acid sequence represented by SEQ ID NO: 12.

In one embodiment, the anti-human MUC1 antibody Fab fragment of the present invention is an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12.

Any constant region of Igγ1, Igγ2, Igγ3 or Igγ4, etc. can be selectable as the heavy chain constant region of the anti-human MUC1 antibody Fab fragment of the present invention. In one embodiment, the heavy chain constant region of the anti-human MUC1 antibody Fab fragment of the present invention is a human Igγ1 constant region.

Any constant region of Igλ or Igκ can be selectable as the light chain constant region of the anti-human MUC1 antibody Fab fragment of the present invention. In one embodiment, the light chain constant region of the anti-human MUC1 antibody Fab fragment of the present invention is a human Igκ constant region.

In one embodiment, the anti-human MUC1 antibody Fab fragment of the present invention is the following Fab fragment:

an anti-human MUC1 antibody Fab fragment comprising a heavy chain fragment consisting of the amino acid sequence represented by SEQ ID NO: 2 or SEQ ID NO: 4 and a light chain consisting of the amino acid sequence represented by SEQ ID NO: 6.

In one embodiment, the anti-human MUC1 antibody Fab fragment of the present invention is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6.

In the case of expressing an antibody including a Fab fragment in cells, the antibody is known to undergo a posttranslational modification. Examples of the posttranslational modification include the cleavage of heavy chain C-terminal lysine by carboxypeptidase, the modification of heavy chain and light chain N-terminal glutamine or glutamic acid into pyroglutamic acid by pyroglutamylation, glycosylation, oxidation, deamidation, and glycation. Such a posttranslational modification is known to occur in various antibodies (J. Pharm. Sci., 2008; 97: 2426-2447).

The anti-human MUC1 antibody Fab fragment of the present invention can also include a Fab fragment resulting from the posttranslational modification. Examples of the anti-human MUC1 antibody Fab fragment of the present invention resulting from the posttranslational modification include an anti-human MUC1 antibody Fab fragment having an N-terminally pyroglutamylated heavy chain. It is known in the art that such a posttranslational modification by N-terminal pyroglutamylation has no influence on the activity of the antibody (Anal. Biochem., 2006; 348: 24-39).

In one embodiment, the anti-human MUC1 antibody Fab fragment of the present invention is an anti-human MUC1 antibody Fab fragment having the following feature:

an anti-human MUC1 antibody Fab fragment comprising a heavy chain fragment comprising a heavy chain variable region derived from a heavy chain variable region consisting of the amino acid sequence represented by SEQ ID NO: 8 or SEQ ID NO: 10 by the modification of glutamine at amino acid position 1 of SEQ ID NO: 8 or SEQ ID NO: 10 into pyroglutamic acid, and a light chain comprising a light chain variable region consisting of the amino acid sequence represented by SEQ ID NO: 12.

In a certain embodiment, the anti-human MUC1 antibody Fab fragment of the present invention is an anti-human MUC1 antibody Fab fragment having the following feature:

an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12.

In an alternative embodiment, the anti-MUC1 antibody Fab fragment of the present invention is an anti-human MUC1 antibody Fab fragment having the following feature:

an anti-human MUC1 antibody Fab fragment comprising a heavy chain fragment derived from a heavy chain fragment consisting of the amino acid sequence represented by SEQ ID NO: 2 or SEQ ID NO: 4 by the modification of glutamine at amino acid position 1 of SEQ ID NO: 2 or SEQ ID NO: 4 into pyroglutamic acid, and a light chain consisting of the amino acid sequence represented by SEQ ID NO: 6.

In a certain embodiment, the anti-MUC1 antibody Fab fragment of the present invention is an anti-human MUC1 antibody Fab fragment having the following feature:

an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

The anti-human MUC1 antibody Fab fragment of the present invention binds to human cancer-specific MUC1. The cancer-specific MUC1 is expressed in cancers such as breast cancer, lung cancer, colorectal cancer, bladder cancer, skin cancer, thyroid gland cancer, stomach cancer, pancreatic cancer, kidney cancer, ovary cancer or uterine cervical cancer. A method for measuring the binding activity of the obtained anti-human MUC1 antibody Fab fragment against human cancer-specific MUC1 includes methods such as ELISA and FACS. In the case of using, for example, ELISA, human cancer-specific MUC1-positive cells (e.g., T-47D cells) are immobilized onto an ELISA plate, to which the Fab fragment is then added and reacted, and then, an anti-Igκ antibody or the like labeled with horseradish peroxidase or the like is reacted. Then, the binding of the secondary antibody is identified by activity measurement using a reagent for detecting the activity thereof (e.g., a chemiluminescent horseradish peroxidase substrate for the horseradish peroxidase label) or the like.

The anti-human MUC1 antibody Fab fragment of the present invention can be readily prepared by those skilled in the art using a method known in the art on the basis of sequence information on the heavy chain fragment and the light chain of the anti-human MUC1 antibody Fab fragment of the present invention disclosed herein. The anti-human MUC1 antibody Fab fragment of the present invention can be produced according to, but not particularly limited to, a method described in, for example, <Method for producing anti-human MUC1 antibody Fab fragment according to present invention> mentioned later.

<Conjugate of Present Invention>

The conjugate of the present invention is a conjugate comprising a labeling moiety and the anti-human MUC1 antibody Fab fragment of the present invention.

The "labeling moiety" is (i) a ligand and a linker, (ii) a ligand, (iii) a fluorescent dye and a linker, or (iv) a fluorescent dye. A certain embodiment is (i) a ligand and a linker, or (ii) a ligand. A certain embodiment is (i) a fluorescent dye and a linker, or (ii) a fluorescent dye. The ligand of the "labeling moiety" may further comprise a metal. A certain embodiment is (i) a ligand and a linker or (ii) a ligand comprising a metal, and in other words, is (i) a ligand that has formed a chelate complex with a metal, and a linker, or (ii) a ligand that has formed a chelate complex with a metal.

The conjugate of the present invention comprising a metal or a fluorescent dye can be used in various contrast media and/or cancer therapeutic agents and is used in, for example, an MRI contrast medium, a PET tracer, a fluorescently labeled molecular imaging agent, and a drug for use in photoimmunotherapy methods.

In the present specification, the "metal" means a paramagnetic metal ion or a metal radioisotope.

The paramagnetic metal ion is suitably used in an MRI contrast medium.

Examples of the embodiment of the paramagnetic metal ion include, but are not limited to, $Fe^{2+}$, $Fe^{3+}$, $Cu^{2+}$, $Ni^{2+}$, $Rh^{2+}$, $Co^{2+}$, $Gd^{3+}$, $Eu^{3+}$, $Dy^{3+}$, $Tb^{3+}$, $Pm^{3+}$, $Nd^{3+}$, $Tm^{3+}$, $Ce^{3+}$, $Y^{3+}$, $Ho^{3+}$, $Er^{3+}$, $La^{3+}$, $Yb^{3}$, $Mn^{3+}$, and $Mn^{2+}$. A certain embodiment is $Gd^{3+}$, $Mn^{3+}$, $Mn^{2+}$, $Fe^{2+}$, or $Fe^{3+}$. A certain embodiment is $Mn^{3+}$ or $Mn^{2+}$. In this case, halogen or the like can be used as a counter anion in the conjugate. Alternatively, the counter anion may be $C(=O)O^-$ of the ligand. The conjugate may further have a counter cation such as $Na^+$.

The metal radioisotope is used in, for example, a PET tracer. Examples of a certain embodiment include, but are not limited to, $^{89}Zr$, $^{51}Mn$, $^{52}Fe$, $^{60}Cu$, $^{67}Ga$, $^{68}Ga$, $^{72}As$, $^{99m}Tc$, and $^{111}In$. A certain embodiment is $^{89}Zr$, 60Cu, $^{67}Ga$, $^{68}Ga$, $^{99m}Tc$, or $^{111}In$. A certain embodiment is a radioisotope of zirconium. A certain embodiment is $^{89}Zr$.

The "ligand" is a moiety capable of forming a chelate complex with a metal in the conjugate and means a group constituted by a chelating agent. The constituted group is a group having a bond by the removal of a proton from the chelating agent.

The "chelating agent" is a compound that can form a coordinate bond with a metal.

Examples of the "chelating agent" include siderophore and non-siderophore. Examples of the siderophore include hydroxamic acid type, catechol type, and mixed ligand type. Examples of the hydroxamic acid-type siderophore include ferrichrome, deferoxamine (DFO) represented by the following formula:

[Formula 5]

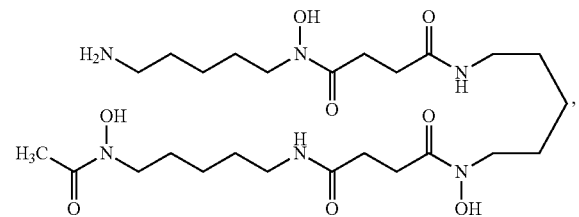

fusarinine C, ornibactin, and rhodotorulic acid. Examples of the catechol-type siderophore include enterobactin, bacillibactin, and vibriobactin. Examples of the mixed ligand-type siderophore include azotobactin, pyoverdine, and yersiniabactin. In the case of the siderophore, DFO can be reacted via its reactive functional group —$NH_2$ with the linker or the Fab fragment, and the siderophore other than DFO can also be reacted via its reactive functional group such as a carboxy group, a hydroxy group, or an amino group with the linker or the Fab fragment by a method usually used by those skilled in the art.

Examples of the non-siderophore include DTPA (diethylenetriaminepentaacetic acid, CAS No: 67-43-6), DTPA-BMA (1,7-bis(methylcarbamoylmethyl)-1,4,7-triazaheptane-1,4,7-triacetic acid, CAS No: 119895-95-3), EOB-DTPA (DTPA bound to an ethoxybenzyl group, CAS No: 158599-72-5), TTHA (triethylenetetraminehexaacetic acid, CAS No: 869-52-3), DO3A (1,4,7,10-tetraazacyclododecane-1,4,7-triacetic acid, CAS No: 217973-03-0), HP-DO3A (10-(2-hydroxypropyl)-1,4,7,10-tetraazacyclododecane-1,4,7-triacetic acid, CAS No: 120041-08-9), DOTA (1,4,7,10-tetraazacyclododecane-1,4,7,10-tetraacetic acid, CAS No: 60239-18-1), and known reactive derivatives thereof.

Compounds and conjugates described herein also encompass free forms and salts thereof unless otherwise specified. In this context, the "salt thereof" is a salt that can be formed by the compound or the conjugate that may form an acid-addition salt or a salt with a base depending on the type of a substituent in the compound or the conjugate. Specific examples thereof include: acid-addition salts with inorganic acids such as hydrochloric acid, hydrobromic acid, hydroiodic acid, sulfuric acid, nitric acid, and phosphoric acid, or organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid; salts with inorganic bases such as sodium, potassium, magnesium, calcium, and aluminum, or organic bases such as methylamine, ethylamine, ethanolamine, lysine, and ornithine; salts with various amino acids and amino acid derivatives, such as acetylleucine; and ammonium salts. For example, DFO exists as deferoxamine methanesulfonate or exists as other salts. DTPA exits both as a free form and as sodium salt.

A certain embodiment of the "chelating agent" for use in an MRI contrast medium is the siderophore or non-siderophore chelating agent described above.

A certain embodiment of the "chelating agent" for use in a PET tracer is the siderophore or non-siderophore chelating agent described above. A certain embodiment is MAG3 (mercapto-acetyl-glycine-glycine-glycine, CAS No: 66516-09-4). A certain embodiment is DFO.

Examples of a certain embodiment of the "chelating agent" constituting the ligand contained in the conjugate of the present invention include DFO, DTPA, DTPA-BMA, EOB-DTPA, DO3A, HP-DO3A, and DOTA. A certain embodiment is DFO, DTPA, or DOTA. A certain embodiment is DFO.

The "linker is a group that creates a distance between the anti-human MUC1 antibody Fab fragment and the ligand. Examples of a certain embodiment of the "linker" in the conjugate include the following formula:

[Formula 6]

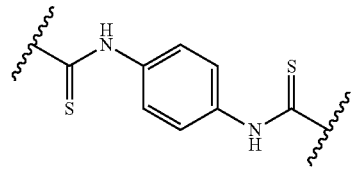

(hereinafter, referred to as —C(=S)—NH-(1,4-phenylene)-NH—C(=S)—), —CH$_2$-(1,4-phenylene)-NH—C(=S)—, and —C(=O)—(C$_{1-20}$ alkylene)-C(=O)—. In this context, the "C$_{1-20}$ alkylene" is linear or branched alkylene having 1 to 20 carbon atoms. A certain embodiment of the C$_{1-20}$ alkylene is C$_{1-10}$ alkylene or C$_{1-2}$ alkylene. A certain embodiment of the C$_{1-20}$ alkylene is ethylene. A certain embodiment is —C(=S)—NH-(1,4-phenylene)-NH—C(=S)—. A certain embodiment is —C(=O)—C$_2$H$_4$—C(=O)—. Examples of a reagent that can be used as the linker include HO—C(=O)—(C$_{1-20}$ alkylene)-C(=O)—OH, succinic acid, and p-di-NCS-benzene(p-diisocyanobenzene).

The conjugate of the present invention comprising a fluorescent dye can be used as a fluorescently labeled molecular imaging agent, a drug for use in photoimmunotherapy methods, or a fluorescently labeled molecular imaging agent and a drug for use in photoimmunotherapy methods.

A dye having absorption maximum and emission maximum at a near-infrared wavelength (650 to 1000 nm) usually used in photoimaging can be used as the fluorescent dye for use in the conjugate of the present invention. Examples of a certain embodiment of the fluorescent dye include cyanine and indocyanine compounds. Examples of a certain embodiment include IRDye800CW and IRDye700DX (LI-COR Bioscience, Inc.), Cy (Molecular Probes, Inc.), Alexa Fluor, BODIPY, and DyLight (Thermo Fisher Scientific Inc.), CF790 (Biotium, Inc.), DY (Dyomics GmbH), HiLyte Fluor 680 and HiLyte Fluor 750 (AnaSpec Inc.), and PULSAR650 and QUASAR670 (LGC Biosearch Technologies). A certain embodiment is IRDye800CW represented by the following formula:

[Formula 7]

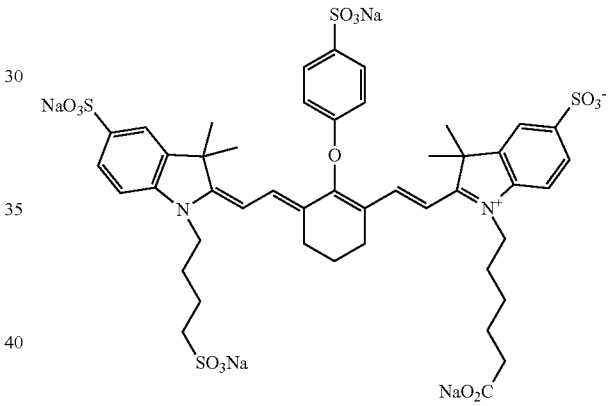

or IRDye700DX represented by the following formula:

[Formula 8]

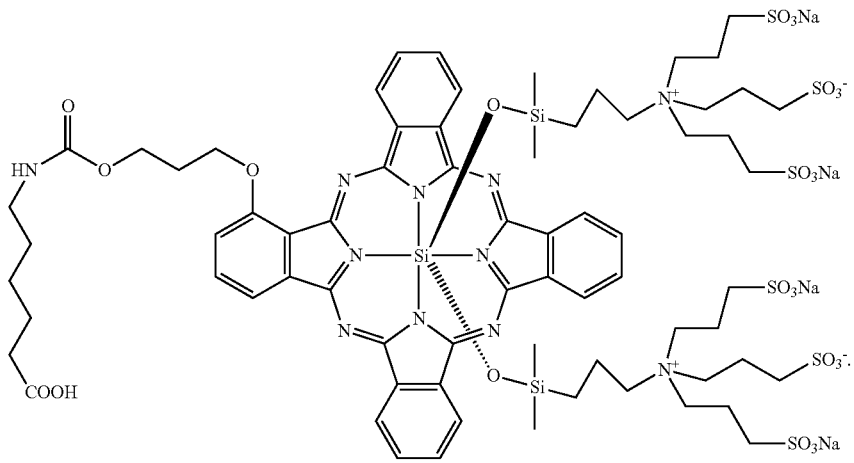

The fluorescent dye can be reacted via its carboxy group, hydroxy group, amino group, or the like or via an active group introduced by a method usually used by those skilled in the art with the Fab fragment or the linker. A certain embodiment of the fluorescent dye having an introduced active group is a fluorescent dye esterified with a N-hydroxysuccinimide (NHS) group. For example, NHS esters of IRDye800CW and IRDye700DX mentioned above are commercially available, and they can be utilized.

The binding of the anti-human MUC1 antibody Fab fragment of the present invention to the labeling moiety can be appropriately performed by those skilled in the art using a known approach. For example, the labeling moiety can be bound to one or more amino groups (e.g., a N-terminal amino group and an amino group of an amino acid side chain), one or more thiol groups (e.g., a thiol group of an amino acid side chain), or one or more carboxyl groups (e.g., carboxyl groups of the C terminus and an amino acid side chain) of the anti-human MUC1 antibody Fab fragment of the present invention. A certain embodiment of the conjugate of the present invention is a conjugate wherein the labeling moiety is bound to one or more amino groups of the anti-human MUC1 antibody Fab fragment of the present invention.

When the labeling moiety is a ligand and a linker, the conjugate of the present invention may be produced by reacting the chelating agent with a substance obtained through the reaction of the anti-human MUC1 antibody Fab fragment of the present invention with the linker. It may be produced by reacting the anti-human MUC1 antibody Fab fragment of the present invention with a substance obtained through the reaction of the chelating agent with the linker. As a reaction example, a substance obtained through the reaction of the amino group of the chelating agent with the linker may be reacted with one or more amino groups (e.g., an N-terminal amino group and an amino group of a lysine side chain) of the anti-human MUC1 antibody Fab fragment of the present invention. Reaction of synthesizing thiourea by adding isothiocyanate to amine, reaction of synthesizing amide by adding amine and carboxylic acid, or the like can be used in the production of the conjugate. The reaction can be performed by the application of a method known to those skilled in the art. A compound of the chelating agent bound to the linker in advance may be used as a starting material. Examples of the compound of the chelating agent bound to the linker include p-SCN-Bn-DFO (DFO bound to a p-isothiocyanophenylaminothiocarbonyl group, CAS No: 1222468-90-7) represented by the following formula:

[Formula 9]

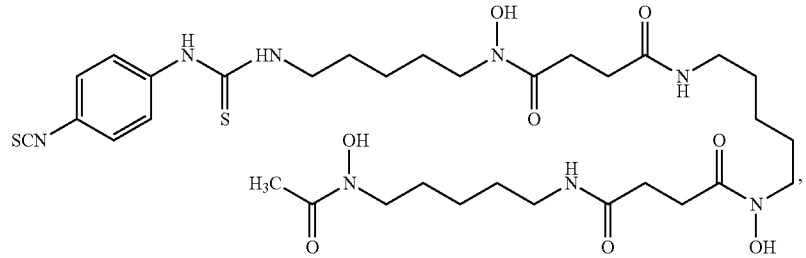

DTPA bound to a p-isothiocyanobenzyl group (p-NCS-Bn-DTPA, CAS No: 102650-30-6), DOTA bound to a p-isothiocyanobenzyl group (p-NCS-Bn-DOTA, CAS No: 127985-74-4), and p-SCN-Bn-CHX-A"-DTPA ([(R)-2-amino-3-(4-isothiocyanatophenyl)propyl]-trans-(S,S)-cyclohexane-1,2-diamine-pentaacetic acid, CAS No: 157380-45-5).

The metal (paramagnetic metal ion or metal radioisotope) can be added to the anti-human MUC1 antibody Fab fragment of the present invention bound to one or more labeling moiety thus produced by the production method to obtain the conjugate of the present invention comprising the metal.

Also, the conjugate of the present invention may be produced as a conjugate which is a Fab fragment bound via an amino group thereof to one or more labeling moiety by reacting one or more amino groups (e.g., a N-terminal amino group and an amino group of an amino acid side chain) of the Fab fragment with the labeling moiety having a carboxyl group or an isothiocyanic acid group activated with N-hydroxysuccinimide (NHS).

The conjugate of the present invention is a conjugate comprising one or more labeling moiety and the anti-human MUC1 antibody Fab fragment of the present invention. A certain embodiment is the anti-human MUC1 antibody Fab fragment bound to 1 to 27 labeling moieties. A certain embodiment is the anti-human MUC1 antibody Fab fragment bound to 1 to 23 labeling moieties. A certain embodiment is the anti-human MUC1 antibody Fab fragment bound to 1 to 15 labeling moieties. A certain embodiment is the anti-human MUC1 antibody Fab fragment bound to 1 to 11 labeling moieties. A certain embodiment is the anti-human MUC1 antibody Fab fragment bound to 1 to 9 labeling moieties. A certain embodiment is the anti-human MUC1 antibody Fab fragment bound to 1 to 7 labeling moieties. A certain embodiment is the anti-human MUC1 antibody Fab fragment bound to 1 to 5 labeling moieties. A certain embodiment is the anti-human MUC1 antibody Fab fragment bound to 1 to 4 labeling moieties. A certain embodiment is the anti-human MUC1 antibody Fab fragment bound to one or more labeling moiety further comprising a metal.

In one embodiment, the conjugate of the present invention is a conjugate wherein the labeling moiety is (i) a ligand and a linker, (ii) a ligand, (iii) a fluorescent dye and a linker, or (iv) a fluorescent dye.

In a certain embodiment, examples of the conjugate of the present invention include the followings:

(1) a conjugate wherein the anti-human MUC1 antibody Fab fragment is an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12;

(2) the conjugate of (1), wherein the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6;

(3) a conjugate wherein the anti-human MUC1 antibody Fab fragment is an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12;

(4) the conjugate of (2), wherein the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6;

(5) the conjugate of any of (1) to (4), wherein the labeling moiety is (i) a ligand and a linker, or (ii) a ligand;

(6) the conjugate of any of (1) to (4), wherein the ligand is a group constituted by a chelating agent selected from the group consisting of DFO, DTPA, DTPA-BMA, EOB-DTPA, DO3A, HP-DO3A and DOTA, and the linker is a linker selected from the group consisting of —C(=S)—NH-(1,4-phenylene)-NH—C(=S)—, —CH$_2$-(1,4-phenylene)-NH—C(=S)— and —C(=O)—(C$_{1-20}$ alkylene)-C(=O)—;

(7) the conjugate of (6), wherein the ligand is a group constituted by a chelating agent selected from the group consisting of DFO, DTPA, and DOTA;

(8) the conjugate of (6), wherein the ligand is a group constituted by DFO, and the linker is —C(=S)—NH-(1,4-phenylene)-NH—C(=S)—;

(9) the conjugate according to any of (5) to (8), further comprising a metal;

(10) the conjugate of (9), wherein the metal is a metal radioisotope; and

(11) the conjugate of (10), wherein the metal is $^{89}$Zr.

In a certain embodiment, the conjugate of the present invention is a conjugate wherein the labeling moiety is (i) a ligand and a linker, or (ii) a ligand.

In a certain embodiment, the conjugate of the present invention is a conjugate wherein the ligand is a ligand represented by the following formula (A):

[Formula 10]

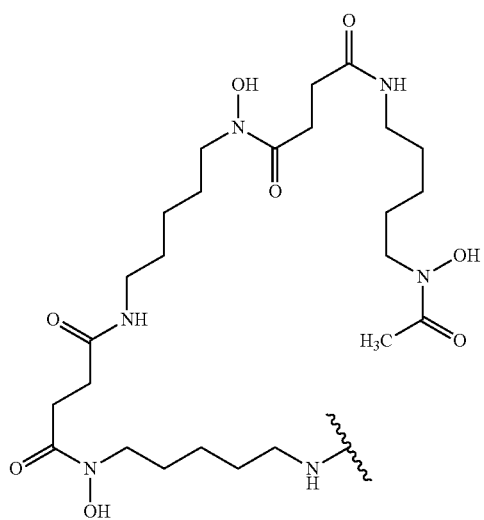

(A)

wherein the wavy line represents binding to the anti-human MUC1 antibody Fab fragment or the linker.

In a certain embodiment, the conjugate of the present invention wherein the ligand is a ligand represented by formula (A) is a conjugate wherein the labeling moiety is a ligand and a linker represented by the following formula (A'):

[Formula 11]

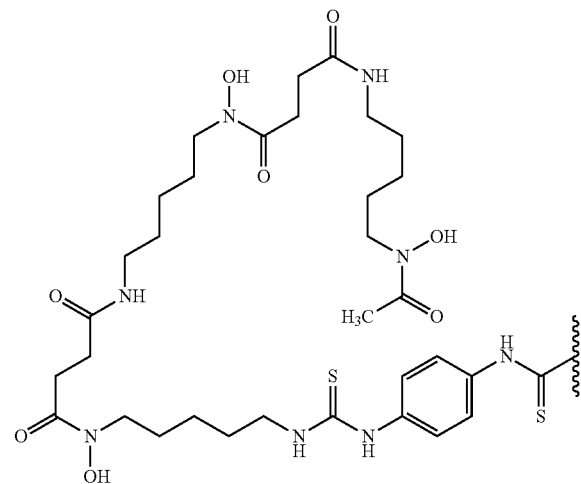

(A')

wherein the wavy line represents binding to the anti-human MUC1 antibody Fab fragment, and the anti-human MUC1 antibody Fab fragment is bound via an amino group thereof to the carbon atom of a labeling moiety terminal C(=S) group.

In a certain embodiment, the conjugate of the present invention is a conjugate wherein the labeling moiety is (i) a ligand and a linker, or (ii) a ligand, the conjugate further comprising a metal. A certain embodiment of the metal is a metal radioisotope. A certain embodiment of the metal radioisotope is $^{89}$Zr.

In an alternative embodiment, the conjugate of the present invention is a conjugate wherein the labeling moiety is (i) a fluorescent dye and a linker, or (ii) a fluorescent dye.

In a certain embodiment, the conjugate of the present invention wherein the labeling moiety comprises a fluorescent dye is a conjugate wherein the fluorescent dye is a fluorescent dye selected from the group consisting of the following formula (B) and the following formula (C):

[Formula 12]

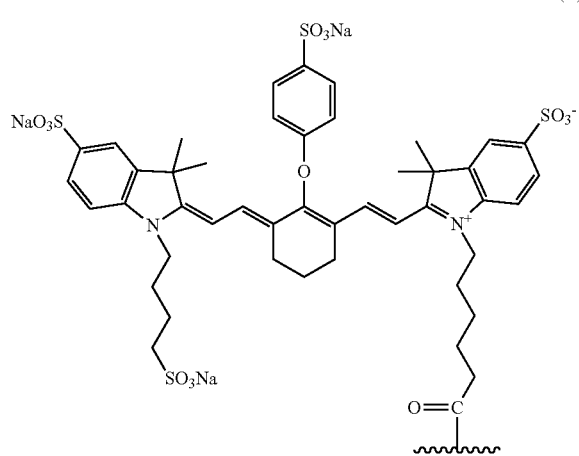

(B)

[Formula 13]

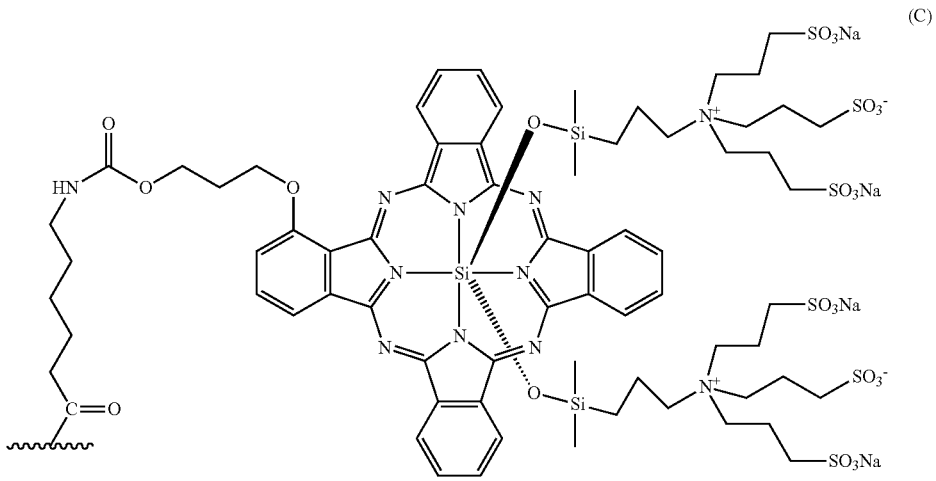

(C)

wherein the wavy line represents binding to the anti-human MUC1 antibody Fab fragment or the linker.

In a certain embodiment, the conjugate of the present invention wherein the labeling moiety is a fluorescent dye represented by formula (B) is a conjugate wherein the wavy line represents binding to the anti-human MUC1 antibody Fab fragment, and the anti-human MUC1 antibody Fab fragment is bound via an amino group thereof to the carbon atom of a labeling moiety terminal C(=O) group.

In a certain embodiment, the conjugate of the present invention wherein the labeling moiety is a fluorescent dye represented by formula (C) is a conjugate wherein the wavy line represents binding to the anti-human MUC1 antibody Fab fragment, and the anti-human MUC1 antibody Fab fragment is bound via an amino group thereof to the carbon atom of a labeling moiety terminal C(=O) group.

Certain embodiments of the conjugate of the present invention will be further shown below:

(1) a conjugate wherein the labeling moiety is a ligand and a linker represented by formula (A'), and the anti-human MUC1 antibody Fab fragment is an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12;

(2) the conjugate of (1), wherein the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6;

(3) a conjugate wherein the labeling moiety is a ligand and a linker represented by formula (A'), and the anti-human MUC1 antibody Fab fragment is an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12;

(4) the conjugate of (3), wherein the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6;

(5) the conjugate of (2) or (4) which is the anti-human MUC1 antibody Fab fragment bound to 1 to 11 labeling moieties;

(6) the conjugate of (2) or (4) which is the anti-human MUC1 antibody Fab fragment bound to 1 to 4 labeling moieties;

(7) the conjugate of any of (1) to (6), further comprising a metal;

(8) the conjugate of (7), wherein the metal is a metal radioisotope;

(9) the conjugate of (8), wherein the metal is $^{89}$Zr;

(10) a conjugate wherein the labeling moiety is a fluorescent dye represented by formula (B) or formula (C), and the anti-human MUC1 antibody Fab fragment is an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12;
(11) the conjugate of (10), wherein the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6;
(12) a conjugate wherein the labeling moiety is a fluorescent dye represented by formula (B) or formula (C), and the anti-human MUC1 antibody Fab fragment is an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12;
(13) the conjugate of (12), wherein the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6;
(14) the conjugate of any of (10) to (13), wherein the labeling moiety is a fluorescent dye represented by formula (C);
(15) the conjugate of (14) which is the anti-human MUC1 antibody Fab fragment bound to 1 to 11 labeling moieties;
(16) the conjugate of (15) which is the anti-human MUC1 antibody Fab fragment bound to 1 to 5 labeling moieties;
(17) the conjugate of any of (10) to (13), wherein the labeling moiety is a fluorescent dye represented by formula (B);
(18) the conjugate of (17) which is the anti-human MUC1 antibody Fab fragment bound to 1 to 11 labeling moieties; and
(19) the conjugate of (18) which is the anti-human MUC1 antibody Fab fragment bound to 1 to 5 labeling moieties.

In an alternative embodiment, the conjugate of the present invention is a conjugate represented by the following formula (I):
[Formula 14]

(L-X)$_p$-Ab  (I)

wherein Ab represents the anti-human MUC1 antibody Fab fragment,
L represents (i) a ligand or (ii) a fluorescent dye,
X represents a linker or a bond, and
p is a natural number of 1 to 27. A certain embodiment of p is a natural number of 1 to 23. A certain embodiment is a natural number of 1 to 15. A certain embodiment is a natural number of 1 to 11. A certain embodiment is a natural number of 1 to 9. A certain embodiment is a natural number of 1 to 7. A certain embodiment is a natural number of 1 to 5. A certain embodiment is a natural number of 1 to 4.

In a certain embodiment, the conjugate of the present invention is a conjugate of formula (I), the conjugate further comprising a metal. A certain embodiment of the metal is a metal radioisotope. A certain embodiment of the metal radioisotope is $^{89}$Zr.

In a certain embodiment, the conjugate of formula (I) is the conjugate of the present invention wherein the labeling moiety is a ligand and a linker represented by formula (A'). In a certain embodiment, this conjugate is a conjugate represented by the following formula (II):

[Formula 15]

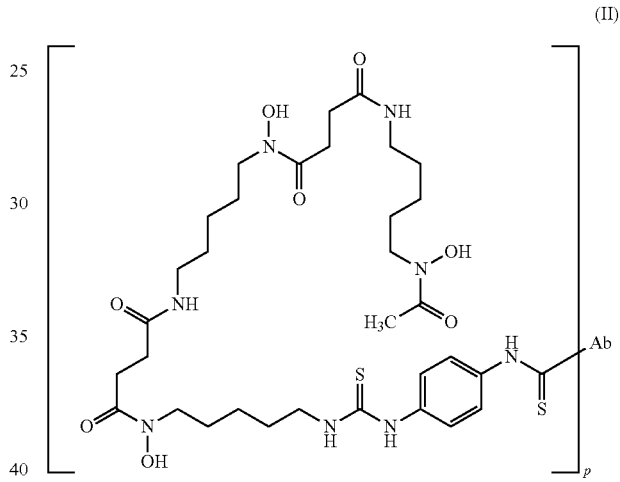

wherein Ab represents the anti-human MUC1 antibody Fab fragment, and
p is a natural number of 1 to 27. A certain embodiment of p is a natural number of 1 to 23. A certain embodiment is a natural number of 1 to 15. A certain embodiment is a natural number of 1 to 11. A certain embodiment is a natural number of 1 to 9. A certain embodiment is a natural number of 1 to 7. A certain embodiment is a natural number of 1 to 5. A certain embodiment is a natural number of 1 to 4.

Ab is bound via an amino group thereof to the carbon atom of a labeling moiety terminal C(=S) group.

In a certain embodiment, the conjugate of formula (II), the conjugate further comprising a metal. A certain embodiment of the metal is a metal radioisotope. A certain embodiment of the metal radioisotope is $^{89}$Zr.

In a certain embodiment, the conjugate of formula (I) is the conjugate of the present invention wherein the labeling moiety is a fluorescent dye represented by formula (B). In a certain embodiment, the conjugate is a conjugate represented by the following formula (III):

[Formula 16]

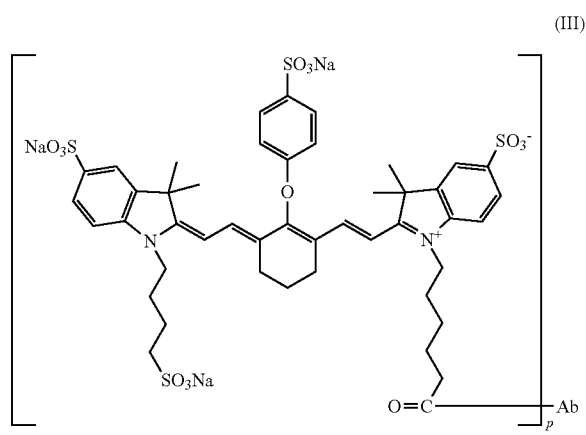

wherein Ab represents the anti-human MUC1 antibody Fab fragment, and
p is a natural number of 1 to 27. A certain embodiment of p is a natural number of 1 to 23. A certain embodiment is a natural number of 1 to 15. A certain embodiment is a natural number of 1 to 11. A certain embodiment is a natural number of 1 to 9. A certain embodiment is a natural number of 1 to 7. A certain embodiment is a natural number of 1 to 5. A certain embodiment is a natural number of 1 to 4.
Ab is bound via an amino group thereof to the carbon atom of a labeling moiety terminal C(=O) group.

In a certain embodiment, the conjugate of formula (I) is the conjugate of the present invention wherein the labeling moiety is a fluorescent dye represented by formula (C). In a certain embodiment, this conjugate is a conjugate represented by the following formula (IV):

7. A certain embodiment is a natural number of 1 to 5. A certain embodiment is a natural number of 1 to 4.
Ab is bound via an amino group thereof to the carbon atom of a labeling moiety terminal C(=O) group.

In a certain embodiment, the conjugate of the present invention is the anti-human MUC1 antibody Fab fragment of the present invention labeled with a detectable molecule. The anti-human MUC1 antibody Fab fragment of the present invention labeled with a detectable molecule is the anti-human MUC1 antibody Fab fragment of the present invention and the detectable molecule linked through a covalent bond directly or via an appropriate linker. In the present specification, the detectable molecule means every moiety detectable in an imaging diagnosis technique known in the art. When the imaging diagnosis technique is, for example, fluorescence imaging, the detectable molecule is a fluorescent dye. When the imaging diagnosis technique is PET, the detectable molecule is a compound imagable by PET. A certain embodiment is a compound comprising a ligand labeled with a radionuclide, or a sugar residue labeled with a nonmetal radionuclide. A certain embodiment of the compound comprising a ligand labeled with a radionuclide is a ligand that has formed a chelate complex with a metal radioisotope. When the imaging diagnosis technique is MRI, the detectable molecule is a compound detectable by the MRI technique. A certain embodiment is a compound comprising a labeled ligand having a paramagnetic metal ion. A certain embodiment of the compound comprising a labeled ligand having a paramagnetic metal ion is a ligand that has formed a chelate complex with a paramagnetic metal ion.

When the anti-human MUC1 antibody Fab fragment of the present invention labeled with a detectable molecule is used in the context of a detectable molecule, the compound imagable by PET is referred to as a PET tracer, and the compound detectable by the MRI technique is referred to as a MRI contrast medium.

[Formula 17]

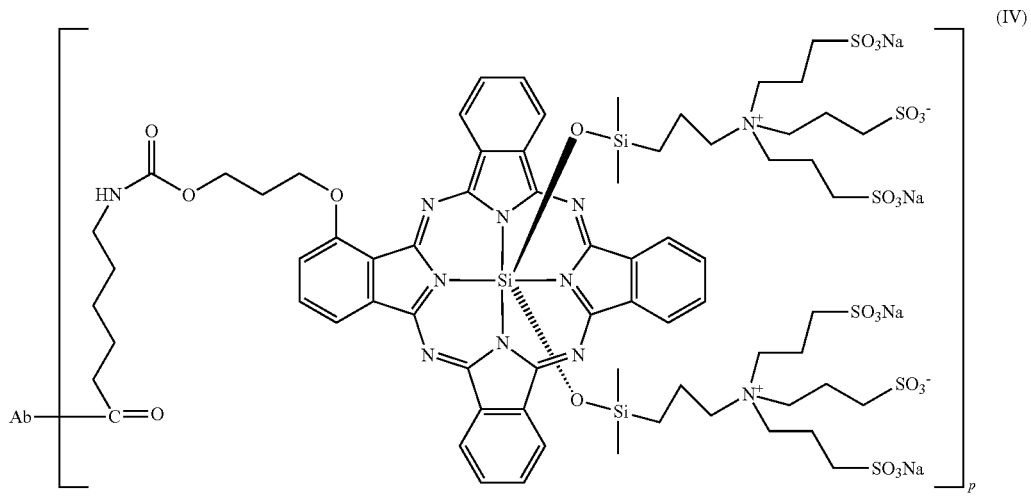

wherein Ab represents the anti-human MUC1 antibody Fab fragment, and
p is a natural number of 1 to 27. A certain embodiment of p is a natural number of 1 to 23. A certain embodiment is a natural number of 1 to 15. A certain embodiment is a natural number of 1 to 11. A certain embodiment is a natural number of 1 to 9. A certain embodiment is a natural number of 1 to Examples of certain embodiments of the anti-human MUC1 antibody Fab fragment of the present invention labeled with a detectable molecule include the followings:
(1) an anti-human MUC antibody Fab fragment wherein the detectable molecule is a fluorescent dye, a PET tracer, or a MRI contrast medium;

(2) the anti-human MUC1 antibody Fab fragment of (1), wherein the detectable molecule is a fluorescent dye;
(3) the anti-human MUC1 antibody Fab fragment of (2), wherein the detectable molecule is a fluorescent dye represented by formula (B);
(4) the anti-human MUC1 antibody Fab fragment of (2), wherein the detectable molecule is a fluorescent dye represented by formula (C);
(5) the anti-human MUC antibody Fab fragment of (1), wherein the detectable molecule is a PET tracer or a MRI contrast medium;
(6) an anti-human MUC1 antibody Fab fragment wherein the detectable molecule is a MRI contrast medium comprising a ligand represented by formula (A) and a paramagnetic metal ion, or a PET tracer comprising the ligand and a metal radioisotope; and
(7) the anti-human MUC1 antibody Fab fragment of (6), wherein the detectable molecule and the linker are a MRI contrast medium comprising a ligand and a linker represented by formula (A') and a paramagnetic metal ion, or a PET tracer comprising the ligand and the linker and a metal radioisotope.

The method mentioned above can be employed for the linking of the anti-human MUC1 antibody Fab fragment of the present invention to the detectable molecule.

The conjugate of the present invention also includes a conjugate which is a mixture of a plurality of conjugates of the present invention. For example, a conjugate which is mixture of a conjugate comprising a labeling moiety and a non-posttranslationally-modified anti-human MUC1 antibody Fab fragment of the present invention, and a conjugate comprising a labeling moiety and the anti-human MUC1 antibody Fab fragment of the present invention resulting from the posttranslational modification of the anti-human MUC1 antibody Fab fragment is also included in the conjugate of the present invention.

Certain embodiments of the conjugate of the present invention which is a mixture of a plurality of conjugates of the present invention will be shown below:
(1) a conjugate which is a mixture of a conjugate wherein the labeling moiety is a ligand and a linker represented by formula (A'), and the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6, and a conjugate wherein the labeling moiety is a ligand and a linker represented by formula (A'), and the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6;
(2) the conjugate of (1), further comprising a metal;
(3) the conjugate of (2), wherein the metal is a metal radioisotope;
(4) the conjugate of (3), wherein the metal is $^{89}Zr$;
(5) a conjugate which is a mixture of a conjugate wherein the labeling moiety is a fluorescent dye represented by formula (B), and the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6, and a conjugate wherein the labeling moiety is a fluorescent dye represented by formula (B), and the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6; and
(6) a conjugate which is a mixture of a conjugate wherein the labeling moiety is a fluorescent dye represented by formula (C), and the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6, and a conjugate wherein the labeling moiety is a fluorescent dye represented by formula (C), and the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

<Polynucleotide of Present Invention>

The polynucleotide of the present invention includes a polynucleotide comprising a nucleotide sequence encoding the heavy chain fragment of the anti-human MUC1 antibody Fab fragment of the present invention, and a polynucleotide comprising a nucleotide sequence encoding the light chain of the anti-human MUC1 antibody Fab fragment of the present invention.

In one embodiment, the polynucleotide of the present invention is a polynucleotide comprising a nucleotide sequence encoding a heavy chain fragment comprising a heavy chain variable region consisting of the amino acid sequence represented by SEQ ID NO: 8, or a polynucleotide comprising a nucleotide sequence encoding a heavy chain fragment comprising a heavy chain variable region consisting of the amino acid sequence represented by SEQ ID NO: 10.

Examples of the polynucleotide comprising a nucleotide sequence encoding a heavy chain fragment comprising a heavy chain variable region consisting of the amino acid sequence represented by SEQ ID NO: 8 include a polynucleotide comprising the nucleotide sequence represented by SEQ ID NO: 7. Examples of the polynucleotide comprising a nucleotide sequence encoding a heavy chain fragment comprising a heavy chain variable region consisting of the amino acid sequence represented by SEQ ID NO: 10 include a polynucleotide comprising the nucleotide sequence represented by SEQ ID NO: 9.

In one embodiment, the polynucleotide of the present invention is a polynucleotide comprising a nucleotide sequence encoding a heavy chain fragment consisting of the amino acid sequence represented by SEQ ID NO: 2 or a polynucleotide comprising a nucleotide sequence encoding a heavy chain fragment consisting of the amino acid sequence represented by SEQ ID NO: 4.

Examples of the polynucleotide comprising a nucleotide sequence encoding a heavy chain fragment consisting of the amino acid sequence represented by SEQ ID NO: 2 include a polynucleotide comprising the nucleotide sequence represented by SEQ ID NO: 1. Examples of the polynucleotide comprising a nucleotide sequence encoding a heavy chain fragment consisting of the amino acid sequence represented by SEQ ID NO: 4 include a polynucleotide comprising the nucleotide sequence represented by SEQ ID NO: 3.

In one embodiment, the polynucleotide of the present invention is a polynucleotide comprising a nucleotide sequence encoding a light chain comprising a light chain variable region consisting of the amino acid sequence represented by SEQ ID NO: 12.

Examples of the polynucleotide comprising a nucleotide sequence encoding a light chain comprising a light chain variable region consisting of the amino acid sequence represented by SEQ ID NO: 12 include a polynucleotide comprising the nucleotide sequence represented by SEQ ID NO: 11.

In one embodiment, the polynucleotide of the present invention is a polynucleotide comprising a nucleotide sequence encoding a light chain consisting of the amino acid sequence represented by SEQ ID NO: 6.

Examples of the polynucleotide comprising a nucleotide sequence encoding a light chain consisting of the amino acid sequence represented by SEQ ID NO: 6 include a polynucleotide comprising the nucleotide sequence represented by SEQ ID NO: 5.

The polynucleotide of the present invention is synthesizable through the use of a gene synthesis method known in the art on the basis of nucleotide sequences designed from the amino acid sequences of the heavy chain fragment and the light chain of the anti-human MUC1 antibody Fab fragment of the present invention. Various methods known to those skilled in the art, such as methods for synthesizing an antibody gene described in International Publication No. WO 90/07861 can be used as such gene synthesis methods.

<Expression Vector of Present Invention>

The expression vector of the present invention includes an expression vector comprising a polynucleotide comprising a nucleotide sequence encoding the heavy chain fragment of the anti-human MUC1 antibody Fab fragment of the present invention, an expression vector comprising a polynucleotide comprising a nucleotide sequence encoding the light chain of the anti-human MUC1 antibody Fab fragment of the present invention, and an expression vector comprising a polynucleotide comprising a nucleotide sequence encoding the heavy chain fragment of the anti-human MUC1 antibody Fab fragment of the present invention and a polynucleotide comprising a nucleotide sequence encoding the light chain of the anti-human MUC1 antibody Fab fragment of the present invention.

The expression vector of the present invention preferably includes an expression vector comprising a polynucleotide comprising a nucleotide sequence encoding a heavy chain fragment consisting of the amino acid sequence represented by SEQ ID NO: 4, an expression vector comprising a polynucleotide comprising a nucleotide sequence encoding a light chain consisting of the amino acid sequence represented by SEQ ID NO: 6, and an expression vector comprising a polynucleotide comprising a nucleotide sequence encoding a heavy chain fragment consisting of the amino acid sequence represented by SEQ ID NO: 4 and a polynucleotide comprising a nucleotide sequence encoding a light chain consisting of the amino acid sequence represented by SEQ ID NO: 6.

The expression vector of the present invention is not particularly limited as long as a polypeptide encoded by the polynucleotide of the present invention can be produced in various host cells of prokaryotic cells and/or eukaryotic cells. Examples of such an expression vector include plasmid vectors and virus vectors (e.g., adenovirus and retrovirus). Preferably, pEE6.4 or pEE12.4 (Lonza Ltd.) can be used.

The expression vector of the present invention can comprise a promoter operably linked to a gene encoding the heavy chain fragment and/or the light chain in the polynucleotide of the present invention. Examples of the promoter for expressing the Fab fragment of the present invention in a host cell include Trp promoter, lac promoter, recA promoter, XPL promoter, lpp promoter, and tac promoter when the host cell is a bacterium of the genus *Escherichia*. Examples of the promoter for expression in yeasts include PH05 promoter, PGK promoter, GAP promoter, and ADH promoter. Examples of the promoter for expression in bacteria of the genus *Bacillus* include SL01 promoter, SP02 promoter, and penP promoter. Examples thereof include promoters derived from viruses such as CMV, RSV, and SV40, retrovirus promoter, actin promoter, EF (elongation factor) 1α promoter, and heat shock promoter when the host is a eukaryotic cell such as a mammalian cell.

In the case of using a bacterium, particularly, *E. coli*, as a host cell, the expression vector of the present invention can further comprise a start codon, a stop codon, a terminator region and a replicable unit. On the other hand, in the case of using a yeast, an animal cell or an insect cell as a host, the expression vector of the present invention can comprise a start codon and a stop codon. In this case, an enhancer sequence, 5' and 3' untranslated regions of a gene encoding the heavy chain fragment and/or the light chain of the present invention, a secretion signal sequence, a splicing junction, a polyadenylation site, or a replicable unit, etc. may be contained therein. Also, a selective marker usually used (e.g., tetracycline resistance gene, ampicillin resistance gene, kanamycin resistance gene, neomycin resistance gene, dihydrofolate reductase gene) may be contained therein according to a purpose.

<Transformed Host Cell of Present Invention>

The transformed host cell of the present invention includes a host cell transformed with the expression vector of the present invention, selected from the group consisting of the following (a) to (d):

(a) a host cell transformed with an expression vector comprising a polynucleotide comprising a nucleotide sequence encoding the heavy chain fragment of the anti-human MUC1 antibody Fab fragment of the present invention;

(b) a host cell transformed with an expression vector comprising a polynucleotide comprising a nucleotide sequence encoding the light chain of the anti-human MUC1 antibody Fab fragment of the present invention;

(c) a host cell transformed with an expression vector comprising a polynucleotide comprising a nucleotide sequence encoding the heavy chain fragment of the anti-human MUC1 antibody Fab fragment of the present invention and a polynucleotide comprising a nucleotide sequence encoding the light chain of the anti-human MUC1 antibody Fab fragment of the present invention; and (d) a host cell transformed with an expression vector comprising a polynucleotide comprising a nucleotide sequence encoding the heavy chain fragment of the anti-human MUC1 antibody Fab fragment of the present invention and an expression vector comprising a polynucleotide comprising a nucleotide sequence encoding the light chain of the anti-human MUC1 antibody Fab fragment of the present invention.

In one embodiment, the transformed host cell of the present invention is a host cell transformed with the expression vector of the present invention, selected from the group consisting of the following (a) to (d):

(a) a host cell transformed with an expression vector comprising a polynucleotide comprising a nucleotide sequence encoding a heavy chain fragment consisting of the amino acid sequence represented by SEQ ID NO: 4;
(b) a host cell transformed with an expression vector comprising a polynucleotide comprising a nucleotide sequence encoding a light chain consisting of the amino acid sequence represented by SEQ ID NO: 6;
(c) a host cell transformed with an expression vector comprising a polynucleotide comprising a nucleotide sequence encoding a heavy chain fragment consisting of the amino acid sequence represented by SEQ ID NO: 4 and a polynucleotide comprising a nucleotide sequence encoding a light chain consisting of the amino acid sequence represented by SEQ ID NO: 6; and
(d) a host cell transformed with an expression vector comprising a polynucleotide comprising a nucleotide sequence encoding a heavy chain fragment consisting of the amino acid sequence represented by SEQ ID NO: 4 and an expression vector comprising a polynucleotide comprising a nucleotide sequence encoding a light chain consisting of the amino acid sequence represented by SEQ ID NO: 6.

The host cell to be transformed is not particularly limited as long as it is compatible with the expression vector used and can be transformed with the expression vector to express the Fab fragment. Examples thereof include various cells such as natural cells and artificially established cells usually used in the technical field of the present invention (e.g., bacteria (bacteria of the genus *Escherichia* and bacteria of the genus *Bacillus*), yeasts (the genus *Saccharomyces*, the genus *Pichia*, etc.), animal cells and insect cells (e.g., Sf9)), and mammalian cell lines (e.g., cultured cells such as CHO-K1SV cells, CHO-DG44 cells, and 293 cells). The transformation itself can be performed by a known method, for example, a calcium phosphate method or an electroporation method.

<Method for Producing Anti-Human MUC1 Antibody Fab Fragment According to Present Invention>

The method for producing an anti-human MUC1 antibody Fab fragment according to the present invention comprises the step of culturing the transformed host cell of the present invention to express the anti-human MUC1 antibody Fab fragment.

In one embodiment, the transformed host cell of the present invention to be cultured in the method for producing an anti-human MUC1 antibody Fab fragment according to the present invention is selected from the group consisting of the following (a) to (c):

(a) a host cell transformed with an expression vector comprising a polynucleotide comprising a nucleotide sequence encoding the heavy chain fragment of the anti-human MUC1 antibody Fab fragment of the present invention and a polynucleotide comprising a nucleotide sequence encoding the light chain of the anti-human MUC1 antibody Fab fragment of the present invention;
(b) a host cell transformed with an expression vector comprising a polynucleotide comprising a nucleotide sequence encoding the heavy chain fragment of the anti-human MUC1 antibody Fab fragment of the present invention and an expression vector comprising a polynucleotide comprising a nucleotide sequence encoding the light chain of the anti-human MUC1 antibody Fab fragment of the present invention; and
(c) a host cell transformed with an expression vector comprising a polynucleotide comprising a nucleotide sequence encoding the heavy chain fragment of the anti-human MUC1 antibody Fab fragment of the present invention, and a host cell transformed with an expression vector comprising a polynucleotide comprising a nucleotide sequence encoding the light chain of the anti-human MUC1 antibody Fab fragment of the present invention.

A certain form of the transformed host cell of the present invention to be cultured in the method for producing an anti-human MUC1 antibody Fab fragment according to the present invention is selected from the group consisting of the following (a) to (c):

(a) a host cell transformed with an expression vector comprising a polynucleotide comprising a nucleotide sequence encoding a heavy chain fragment consisting of the amino acid sequence represented by SEQ ID NO: 4 and a polynucleotide comprising a nucleotide sequence encoding a light chain consisting of the amino acid sequence represented by SEQ ID NO: 6;
(b) a host cell transformed with an expression vector comprising a polynucleotide comprising a nucleotide sequence encoding a heavy chain fragment consisting of the amino acid sequence represented by SEQ ID NO: 4 and an expression vector comprising a polynucleotide comprising a nucleotide sequence encoding a light chain consisting of the amino acid sequence represented by SEQ ID NO: 6; and
(c) a host cell transformed with an expression vector comprising a polynucleotide comprising a nucleotide sequence encoding a heavy chain fragment consisting of the amino acid sequence represented by SEQ ID NO: 4, and a host cell transformed with an expression vector comprising a polynucleotide comprising a nucleotide sequence encoding a light chain consisting of the amino acid sequence represented by SEQ ID NO: 6.

Preferably, the transformed host cell of the present invention used is a host cell transformed with an expression vector comprising a polynucleotide comprising a nucleotide sequence encoding the heavy chain fragment of the anti-human MUC1 antibody Fab fragment of the present invention and a polynucleotide comprising a nucleotide sequence encoding the light chain of the anti-human MUC1 antibody Fab fragment of the present invention, or a host cell transformed with an expression vector comprising a polynucleotide comprising a nucleotide sequence encoding the heavy chain fragment of the anti-human MUC1 antibody Fab fragment of the present invention and an expression vector comprising a polynucleotide comprising a nucleotide sequence encoding the light chain of the anti-human MUC1 antibody Fab fragment of the present invention.

In the method for producing an anti-human MUC1 antibody Fab fragment according to the present invention, the transformed host cell can be cultured in a nutrient medium. The nutrient medium preferably contains a carbon source, an inorganic nitrogen source or an organic nitrogen source necessary for the growth of the transformed host cell. Examples of the carbon source include glucose, dextran, soluble starch, and sucrose. Examples of the inorganic nitrogen source or the organic nitrogen source include ammonium salts, nitrates, amino acids, corn steep liquor, peptone, casein, meat extracts, soymeal, and potato extracts. Also, other nutrients (e.g., inorganic salts (e.g., calcium chloride, sodium dihydrogen phosphate, and magnesium chloride), vitamins, and antibiotics (e.g., tetracycline, neomycin, ampicillin, and kanamycin)) may be contained therein, if desired.

The culture itself of the transformed host cell is performed by a known method. Culture conditions, for example, temperature, medium pH and culture time, are appropriately selected. When the host is, for example, an animal cell, MEM medium (Science; 1952; 122: 501), DMEM medium (Virology; 1959; 8: 396-97), RPMI1640 medium (J. Am. Med. Assoc.; 1967; 199: 519-24), 199 medium (Proc. Soc. Exp. Biol. Med.; 1950; 73:1-8), or the like containing approximately 5 to 20% of fetal bovine serum can be used as a medium. The medium pH is preferably approximately 6 to 8. The culture is usually performed at approximately 30 to 40° C. for approximately 15 to 336 hours, and aeration or stirring can also be performed, if necessary. When the host is an insect cell, examples thereof include Grace's medium (PNAS; 1985; 82: 8404-8) containing fetal bovine serum. Its pH is preferably approximately 5 to 8. The culture is usually performed at approximately 20 to 40° C. for 15 to 100 hours, and aeration or stirring can also be performed, if necessary. When the host is a bacterium, an actinomycete, a yeast, or a filamentous fungus, for example, a liquid medium containing the nutrient source described above is appropriate. A medium of pH 5 to 8 is preferred. When the host is *E. coli*, preferred examples of the medium include LB medium and M9 medium (Miller et al., Exp. Mol. Genet, Cold Spring Harbor Laboratory; 1972: 431). In such a case, the culture can usually be performed at 14 to 43° C. for approximately 3 to 24 hours with aeration or stirring, if necessary. When the host is a bacterium of the genus *Bacillus*, it can usually be performed at 30 to 40° C. for approximately 16 to 96 hours with aeration or stirring, if necessary. When the host is a yeast, examples of the medium include Burkholder minimum medium (PNAS; 1980; 77: 4505-8). Its pH is desirably 5 to 8. The culture is usually performed at approximately 20 to 35° C. for approximately 14 to 144 hours, and aeration or stirring can also be performed, if necessary.

The method for producing an anti-human MUC1 antibody Fab fragment according to the present invention can comprise the step of recovering, preferably isolating or purifying, the expressed anti-human MUC1 antibody Fab fragment, in addition to the step of culturing the transformed host cell of the present invention to express the anti-human MUC1 antibody Fab fragment. Examples of the isolation or purification method include: methods exploiting solubility, such as salting out and a solvent precipitation method; methods exploiting difference in molecular weight, such as dialysis, ultrafiltration, gel filtration, and sodium dodecyl sulfate-polyacrylamide gel electrophoresis; methods exploiting charge, such as ion-exchange chromatography and hydroxylapatite chromatography; methods exploiting specific affinity, such as affinity chromatography; methods exploiting difference in hydrophobicity, such as reverse-phase high-performance liquid chromatography; and methods exploiting difference in isoelectric point, such as isoelectric focusing.

<Method for Producing Conjugate According to Present Invention>

The method for producing a conjugate according to the present invention comprises the step of covalently binding the anti-human MUC1 antibody Fab fragment of the present invention to a labeling moiety. The method for producing a conjugate according to the present invention may also comprise the steps of: culturing the transformed host cell of the present invention to express the anti-human MUC1 antibody Fab fragment; and covalently binding the Fab fragment to a labeling moiety. The method for producing a conjugate according to the present invention may also comprise the steps of: culturing the transformed host cell of the present invention to express the anti-human MUC1 antibody Fab fragment; recovering the expressed Fab fragment; and covalently binding the Fab fragment to a labeling moiety. The method for producing a conjugate according to the present invention may further comprise the step of adding a metal. The linker, chelating agent, metal, or fluorescent dye, etc., and linking method used can employ those described in <Conjugate of present invention>.

In one embodiment, the method for producing a conjugate according to the present invention is a method comprising the steps of: culturing the transformed host cell of the present invention to express the anti-human MUC1 antibody Fab fragment; and covalently binding the Fab fragment to a labeling moiety. A certain embodiment of the method for producing a conjugate according to the present invention is a method comprising the steps of: culturing the transformed host cell of the present invention to express the anti-human MUC1 antibody Fab fragment; recovering the expressed Fab fragment; and covalently binding the Fab fragment to a labeling moiety.

A certain embodiment of the method for producing a conjugate according to the present invention is a method comprising the steps of: culturing the transformed host cell of the present invention to express the anti-human MUC1 antibody Fab fragment; and i) binding the Fab fragment via a linker to a ligand or ii) covalently binding the Fab fragment directly to a ligand. A certain embodiment of the method for producing a conjugate according to the present invention is a method comprising the steps of: culturing the transformed host cell of the present invention to express the anti-human MUC1 antibody Fab fragment; recovering the expressed Fab fragment; and i) binding the Fab fragment via a linker to a ligand or ii) covalently binding the Fab fragment directly to a ligand.

A certain embodiment of the method for producing a conjugate according to the present invention is a method comprising the steps of: culturing the transformed host cell of the present invention to express the anti-human MUC1 antibody Fab fragment; i) binding the Fab fragment via a linker to a ligand or ii) covalently binding the Fab fragment directly to a ligand; and labeling the ligand of the conjugate with a metal (i.e., forming a chelate complex). A certain embodiment of the method for producing a conjugate according to the present invention is a method comprising the steps of: culturing the transformed host cell of the present invention to express the anti-human MUC1 antibody Fab fragment; recovering the expressed Fab fragment; i) binding the Fab fragment via a linker to a ligand or ii) covalently binding the Fab fragment directly to a ligand; and labeling the ligand of the conjugate with a metal.

A certain embodiment of the method for producing a conjugate according to the present invention is a method comprising the steps of: culturing the transformed host cell of the present invention to express the anti-human MUC1 antibody Fab fragment; i) binding the Fab fragment via a linker to a ligand or ii) covalently binding the Fab fragment directly to a ligand; and labeling the ligand of the conjugate with a metal radioisotope (i.e., forming a chelate complex). A certain embodiment of the method for producing a conjugate according to the present invention is a method comprising the steps of: culturing the transformed host cell of the present invention to express the anti-human MUC1 antibody Fab fragment; recovering the expressed Fab fragment; i) binding the Fab fragment via a linker to a ligand or ii) covalently binding the Fab fragment directly to a ligand; and labeling the ligand of the conjugate with a metal radioisotope.

A certain embodiment of the method for producing a conjugate according to the present invention is a method comprising the steps of: culturing the transformed host cell of the present invention to express the anti-human MUC1 antibody Fab fragment; and i) binding the Fab fragment via a linker to a fluorescent dye or ii) covalently binding the Fab fragment directly to a fluorescent dye. A certain embodiment of the method for producing a conjugate according to the present invention is a method comprising the steps of: culturing the transformed host cell of the present invention to express the anti-human MUC1 antibody Fab fragment; recovering the expressed Fab fragment; and i) binding the Fab fragment via a linker to a fluorescent dye or ii) covalently binding the Fab fragment directly to a fluorescent dye.

A certain embodiment of the method for producing a conjugate according to the present invention is a method comprising the steps of: culturing the transformed host cell of the present invention to express the anti-human MUC1 antibody Fab fragment; and labeling the Fab fragment with a detectable molecule. A certain embodiment of the method for producing a conjugate according to the present invention is a method comprising the steps of: culturing the transformed host cell of the present invention to express the anti-human MUC1 antibody Fab fragment; recovering the expressed Fab fragment; and labeling the Fab fragment with a detectable molecule.

The method for producing a conjugate according to the present invention may be carried out as a method comprising two or more of the steps defined above as a series of steps or may be carried out as a method comprising at least one of the steps defined above. For example, a method comprising the step of binding the anti-human MUC1 antibody Fab fragment of the present invention to a labeling moiety, and a method comprising the step of labeling the anti-human MUC1 antibody Fab fragment of the present invention bound to the labeling moiety with a metal are also included in the method for producing a conjugate according to the present invention. Also, the method for producing a conjugate according to the present invention includes a method having a different order of steps. For example, a method comprising labeling a chelating agent with a metal, and then covalently binding the chelating agent to the anti-human MUC1 antibody Fab fragment of the present invention is also included in the method for producing a conjugate according to the present invention.

<Composition for Diagnosis and Diagnosis Method>

The present invention relates to a composition for diagnosis comprising the conjugate of the present invention comprising a metal or a fluorescent dye (hereinafter, referred to as the detectable conjugate of the present invention). The composition for diagnosis of the present invention may comprise one or more conjugate of the present invention. Specifically, the composition for diagnosis of the present invention may comprise one conjugate of the present invention, or may comprise two or more conjugates of the present invention in combination. The detectable conjugate of the present invention can be formulated according to a routine method and utilized as an early diagnostic drug, a staging drug or a intraoperative diagnostic drug (particularly, a cancer diagnostic drug). The intraoperative diagnostic drug means a diagnostic drug capable of identifying a lesion site during operation such as surgery or endoscopic operation and examining its nature. In the case of using the composition for diagnosis of the present invention as an intraoperative diagnostic drug, the composition for diagnosis is administered to a patient, for example, 2 to 32 hours, 6 to 24 hours in a certain embodiment, or 2 hours in another embodiment, before operation.

The early diagnostic drug means a diagnostic drug aimed at performing diagnosis when no condition is observed or at an early stage. For example, for cancers, it means a diagnostic drug that is used when no condition is observed or at stage 0 or stage 1.

The staging drug means a diagnostic drug capable of examining the degree of progression of a condition. For example, for cancers, it means a diagnostic drug capable of examining the stage thereof.

The cancer expected to be able to be diagnosed by the composition for diagnosis of the present invention is a cancer expressing human MUC1. Examples of a certain embodiment include breast cancer, lung cancer, colorectal cancer, bladder cancer, skin cancer, thyroid gland cancer, stomach cancer, pancreatic cancer, kidney cancer, ovary cancer and uterine cervical cancer. Preferably, the cancer is breast cancer or bladder cancer.

The amount of the conjugate of the present invention added for the formulation of the composition for diagnosis of the present invention differs depending on the degree of symptoms or age of a patient, the dosage form of a preparation used, or the binding titer of the Fab fragment, etc. For example, approximately 0.001 mg/kg to 100 mg/kg based on the mass of the Fab fragment can be used per unit body weight of a patient.

Examples of the dosage form of the composition for diagnosis of the present invention can include parenteral agents such as injections and agents for drip infusion. Administration can be performed by intravenous injection, local intramuscular injection to a target tissue, subcutaneous injection, intravesical administration, or the like. For the formulation, a carrier or an additive suitable for these dosage forms can be used in a pharmaceutically acceptable range. The type of the pharmaceutically acceptable carrier or additive is not particularly limited, and a carrier or an additive well known to those skilled in the art can be used.

The present invention also relates to use of the detectable conjugate of the present invention for the production of a composition for the early diagnosis, a composition for the staging or a composition for the intraoperative diagnosis of a cancer. The present invention also relates to the detectable conjugate of the present invention for use in the early diagnosis, staging or intraoperative diagnosis of a cancer.

Further, the present invention also relates to a method for diagnosing a cancer, comprising preoperatively or intraoperatively administering the detectable conjugate of the present invention to a subject. In this context, the "subject" is a human or any of other mammals in need of receiving the diagnosis. A certain embodiment is a human in need of receiving the diagnosis. The effective amount of the detectable conjugate of the present invention in the diagnosis method of the present invention may be the same amount as the effective amount of the conjugate of the present invention for the formulation described above. In the diagnosis method of the present invention, the detectable conjugate of the present invention is preferably administered by local intramuscular injection to a target tissue, subcutaneous injection, or the like. In the diagnosis method of the present invention, in the case of preoperatively administering the conjugate of the present invention, the conjugate is administered to a patient, for example, 2 to 48 hours, 6 to 24 hours in a certain embodiment, and 2 hours in another embodiment before operation.

In an alternative embodiment, the present invention also relates to use of the anti-human MUC1 antibody Fab fragment of the present invention for the production of the conjugate of the present invention. In a certain embodiment, the present invention also relates to use of the anti-human MUC1 antibody Fab fragment of the present invention for the production of a composition for diagnosis comprising the conjugate of the present invention.

As for a embodiment in which the composition for diagnosis of the present invention comprising a metal radioisotope is provided, it may be labeled with the metal radioisotope immediately before use or may be provided as a composition for diagnosis comprising the metal radioisotope.

<Composition for Treatment and Treatment Method>

The present invention includes a pharmaceutical composition comprising one or more conjugate of the present invention and a pharmaceutically acceptable excipient. Specifically, the composition for treatment of the present invention may comprise one conjugate of the present invention, or may comprise two or more conjugates of the present invention in combination. The conjugate of the present invention can be used in the preparation of a pharmaceutical composition by a method usually used using an excipient usually used in the art, i.e., a pharmaceutical excipient, a pharmaceutical carrier, or the like. Examples of the dosage forms of these pharmaceutical compositions include parenteral agents such as injections and agents for drip infusion. Administration can be performed by intravenous injection, subcutaneous injection, intravesical administration, or the like. For the formulation, an excipient, a carrier, an additive, or the like suitable for these dosage forms can be used in a pharmaceutically acceptable range.

The amount of the conjugate of the present invention added for the formulation described above differs depending on the degree of symptoms or age of a patient, the dosage form of a preparation used, or the binding titer of the Fab fragment, etc. For example, approximately 0.001 mg/kg to 100 mg/kg based on the mass of the Fab fragment can be used per unit body weight of a patient.

The pharmaceutical composition comprising the conjugate of the present invention can be used for the treatment of a cancer. The cancer expected to be able to be treated by the pharmaceutical composition comprising the conjugate of the present invention is a cancer expressing human MUC1. Examples thereof include breast cancer, lung cancer, colorectal cancer, bladder cancer, skin cancer, thyroid gland cancer, stomach cancer, pancreatic cancer, kidney cancer, ovary cancer and uterine cervical cancer.

A certain embodiment of the pharmaceutical composition comprising the conjugate of the present invention is a pharmaceutical composition comprising the conjugate comprising a fluorescent dye and can be used in the treatment of a cancer by application to a photoimmunotherapy method. The photoimmunotherapy method is a method of allowing the conjugate comprising a fluorescent dye to specifically accumulate in cancer tissues, followed by irradiation with light having a wavelength exciting the fluorescent dye contained in the conjugate to induce cell death in a cancer-specific manner through the phototoxic effect of the fluorescent dye. In the case of using the conjugate of the present invention comprising a fluorescent dye in the photoimmunotherapy method, the wavelength of the light for irradiation can be a near-infrared wavelength (650 to 1000 nm).

The present invention includes a pharmaceutical composition for treating breast cancer or bladder cancer, comprising the conjugate of the present invention. The present invention also includes a method for treating breast cancer or bladder cancer, comprising the step of administering a therapeutically effective amount of the conjugate of the present invention, which can comprise the step of performing irradiation with light having a near-infrared wavelength (650 to 1000 nm, for example, 660 to 740 nm, for example, 680 nm), in addition to the step described above. A certain embodiment of the dose of light irradiation is at least 1 J/cm$^2$. A certain embodiment is at least 10 J/cm$^2$. A certain embodiment is at least 100 J/cm$^2$. A certain embodiment is 1 to 500 J/cm$^2$. A certain embodiment is 50 to 200 J/cm$^2$. In a certain embodiment, the irradiation may be carried out a plurality of times after administration of the conjugate of the present invention. The present invention also includes a method for inducing the cell death of cancer cells of breast cancer or bladder cancer, comprising the step of administering a therapeutically effective amount of the conjugate of the present invention.

The pharmaceutical composition for treating a cancer can also be used in the diagnosis of a cancer. For example, the pharmaceutical composition for treating breast cancer or bladder cancer can also be used in the diagnosis of the cancer.

The present invention also includes the conjugate of the present invention for use in the treatment of breast cancer or bladder cancer. The present invention further includes use of the conjugate of the present invention for the production of a pharmaceutical composition for treating breast cancer or bladder cancer.

In an alternative embodiment, the present invention also relates to use of the anti-human MUC1 antibody Fab fragment of the present invention for the production of a pharmaceutical composition comprising the conjugate of the present invention.

The present invention is generally described above. Particular Examples will be provided here for reference in order to obtain further understanding. However, these are given for illustrative purposes and do not limit the present invention.

EXAMPLES

Example 1: Preparation of Anti-Human MUC1 Antibody Fab Fragment

Two anti-human MUC1 antibody Fab fragments designated as P10-1 Fab and P10-2 Fab were prepared.

The amino acid sequences of the heavy chain variable regions and the light chain variable regions of P10-1 Fab and P10-2 Fab were specifically designed as sequences expected to improve affinity and not to attenuate affinity even by the binding of a labeling moiety, by using a molecular model of a humanized antibody constructed in accordance with the literature (Proteins, 2014 August; 82 (8): 1624-35) after humanization of a 1B2 antibody, which is a mouse-derived anti-human cancer-specific MUC1 antibody, with reference to the method described in the literature (Front Biosci., 2008 Jan. 1; 13: 1619-33).

GS vector pEE6.4 (Lonza Ltd.) having an insert of a heavy chain fragment gene formed by connecting a gene encoding a signal sequence (MEWSWVFLFFLSVTT-GVHS (SEQ ID NO: 13)) to the 5' side of the heavy chain variable region gene of P10-1 Fab or P10-2 Fab and connecting a human Igγ1 constant region gene (consisting of a nucleotide sequence from nucleotide positions 355 to 669 of SEQ ID NO: 1 or 3) to the 3' side thereof was prepared. Here, in order to express each Fab fragment, a strop codon was inserted to downstream of a codon of Asp at position 221 based on the EU index provided by Kabat et al. (corresponding to Asp at position 222 in the amino acid sequences of SEQ ID NOs: 2 and 4 mentioned later) in the heavy chain constant region gene. Also, GS vector pEE12.4 (Lonza Ltd.) having an insert of a light chain gene formed by connecting a gene encoding a signal sequence (MSVPTQVLGLLLLWLTDARC (SEQ ID NO: 14)) to the 5' side of the common light chain variable region gene of P10-1 Fab and P10-2 Fab and connecting a human x chain constant region gene (consisting of a nucleotide sequence from nucleotide positions 340 to 660 of SEQ ID NO: 5) to the 3' side thereof was prepared.

The expression of each Fab fragment was performed by the method of transient expression. Expi293F cells (Thermo Fisher Scientific Inc.) cultured into approximately 2500000 cells/mL in Expi293 Expression Medium (Thermo Fisher Scientific Inc.) were transfected with the GS vectors of the heavy chain fragment and the light chain mentioned above using ExpiFectamine 293 Transfection Kit (Thermo Fisher Scientific Inc.), and cultured for 8 days. After expression, the culture supernatant was purified using KappaSelect (GE Healthcare Japan Corp.) to obtain each Fab fragment.

The nucleotide sequence of the heavy chain fragment of P10-1 Fab is shown in SEQ ID NO: 1, and the amino acid sequence encoded thereby is shown in SEQ ID NO: 2. The nucleotide sequence of the heavy chain variable region of P10-1 Fab is shown in SEQ ID NO: 7. The amino acid sequence encoded thereby is shown in SEQ ID NO: 8.

The nucleotide sequence of the heavy chain fragment of P10-2 Fab is shown in SEQ ID NO: 3. The amino acid sequence encoded thereby is shown in SEQ ID NO: 4. The nucleotide sequence of the heavy chain variable region of P10-2 Fab is shown in SEQ ID NO: 9. The amino acid sequence encoded thereby is shown in SEQ ID NO: 10.

The light chain is common in P10-1 Fab and P10-2 Fab. The nucleotide sequence thereof is shown in SEQ ID NO: 5. The amino acid sequence encoded thereby is shown in SEQ ID NO: 6. The nucleotide sequence of the light chain variable region of P10-1 Fab and P10-2 Fab is shown in SEQ ID NO: 11. The amino acid sequence encoded thereby is shown in SEQ ID NO: 12.

Example 2: Amino Acid Modification Analysis of Fab Fragment

As a result of analyzing the amino acid modification of purified P10-2 Fab, it was suggested that heavy chain N-terminal glutamine was modified into pyroglutamic acid in a great majority of purified antibodies.

Example 3: Binding Activity Evaluation of Fab Fragment

Binding activity against human cancer-specific MUC1 was compared as to P10-1 Fab and P10-2 Fab expressed by the method mentioned above with a chimeric 1B2 antibody Fab fragment (hereinafter, referred to as 1B2 Fab; prepared by linking a human IgG1 CH1 domain and a w chain CL domain to the VH domain and the VL domain (their sequence information was quoted from Patent Literature 1), respectively, of the 1B2 antibody (Patent Literature 1); for the convenience of linking of the CH1 domain and the CL domain, an alanine residue at position 113 based on the EU index (Kabat et al.) in the VH domain was substituted by a serine residue, and an alanine residue at position 109 based on the EU index (Kabat et al.) in the VL domain was substituted by a threonine residue) by Cell ELISA. Specifically, breast cancer cell line T-47D cells (purchasable from ATCC; HTB-133) expressing human cancer-specific MUC1 were inoculated at $0.75 \times 10^4$ cells per well to a 96-well ELISA plate coated with collagen I, and cultured overnight. Then, the cells were fixed in formalin, and P10-1 Fab, P10-2 Fab or 1B2 Fab described above was reacted therewith. Then, a horseradish peroxidase (HRP)-labeled goat anti-human Igκ antibody (Southern Biotechnology Associates, Inc.) was reacted as a secondary antibody. ECL Prime Western Blotting Detection Reagent (GE Healthcare Japan Corp.) was added thereto for luminescence, and the degree of the luminescence was examined. As a result, as shown in FIG. 1, P10-1 Fab and P10-2 Fab were confirmed to have approximately 10 or more times the binding activity against human cancer-specific MUC1 compared to 1B2 Fab.

Example 4: Fluorescent Labeling of Fab Fragment

Subsequently, the present inventors labeled P10-1 Fab, P10-2 Fab and 1B2 Fab with a fluorescent dye mentioned above.

Specifically, each Fab fragment solution adjusted to approximately 1 mg/mL with phosphate-buffered saline (pH 7.4) was adjusted to pH 8.5 by the addition of a ¹/₁₀ amount of a 1 M dipotassium hydrogen phosphate solution (pH 9). IRDye800CW NHS Ester (LI-COR Bioscience, Inc.) was added thereto at a final concentration of 310.8 µg/mL, and the resultant was stirred at room temperature under shading for 2 hours. IRDye800CW NHS Ester has a N-hydroxysuccinimide group and therefore reacts immediately with Lys of the Fab fragment. This was recovered through Amicon Ultra 3K-0.5 mL centrifugal filter (Merck Millipore) to purify a fluorescently labeled Fab fragment. P10-1 Fab, P10-2 Fab and 1B2 Fab harboring this fluorescent dye were designated as P10-1 Fab Dye, P10-2 Fab Dye and 1B2 Fab Dye.

Example 5: Binding Activity Evaluation of Fluorescently Labeled Fab Fragment

Figure 2:
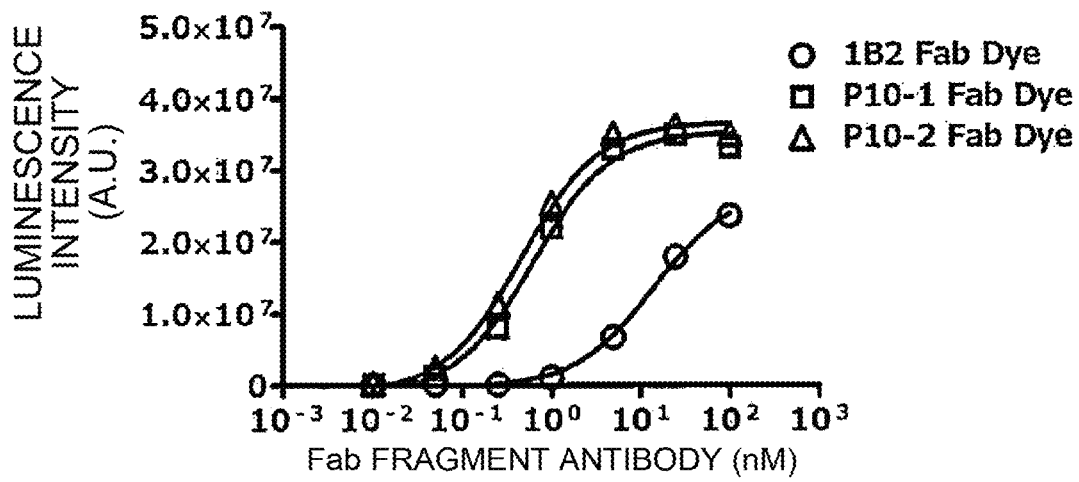
FIG. 2 is a graph and a table showing the binding activity of P10-1 Fab Dye, P10-2 Fab Dye and 1B2 Fab Dye of Comparative Example against human cancer-specific MUC1.

Binding activity against human cancer-specific MUC1 was compared as to P10-1 Fab Dye and P10-2 Fab Dye labeled by the method mentioned above with 1B2 Fab Dye by Cell ELISA. Specifically, breast cancer cell line T-47D cells expressing human cancer-specific MUC1 were inoculated at $0.75 \times 10^4$ cells per well to a 96-well ELISA plate coated with collagen I, and cultured overnight. Then, the cells were fixed in formalin, and P10-1 Fab Dye, P10-2 Fab Dye or 1B2 Fab Dye described above was reacted therewith. Then, a HRP-labeled goat anti-human Igκ antibody (Southern Biotechnology Associates, Inc.) was reacted as a secondary antibody. ECL Prime Western Blotting Detection Reagent (GE Healthcare Japan Corp.) was added thereto for luminescence, and the degree of the luminescence was examined. As a result, as shown in FIG. 2, the binding activity of 1B2 Fab Dye was attenuated by labeling, whereas P10-1 Fab Dye and P10-2 Fab Dye were confirmed to be free from the attenuation of the binding activity by labeling.

Example 6: Labeling of Fab Fragment with Chelating Agent

Subsequently, the present inventors labeled P10-2 Fab with a chelating agent mentioned above.

Specifically, a Fab fragment solution adjusted to 12.5 mg/mL with phosphate-buffered saline (pH 7.4) was adjusted to pH 9.0 by the addition of a 100 M sodium carbonate solution at 10 mM. p-SCN-Bn-deferoxamine (Macrocyclics, Inc.) was added thereto at a final concentration of 1 mM, and the resultant was reacted at 37° C. for 2 hours. p-SCN-Bn-deferoxamine has an isothiocyanate group and therefore reacts immediately with Lys of the Fab fragment. This was recovered through Amicon Ultra 10K-0.5 mL centrifugal filter to purify a chelating agent-labeled Fab fragment. This chelating agent-labeled P10-2 Fab was designated as P10-2 Fab DFO.

Example 7: Binding Activity Evaluation of Chelating Agent-Labeled Fab Fragment

Figure 3:
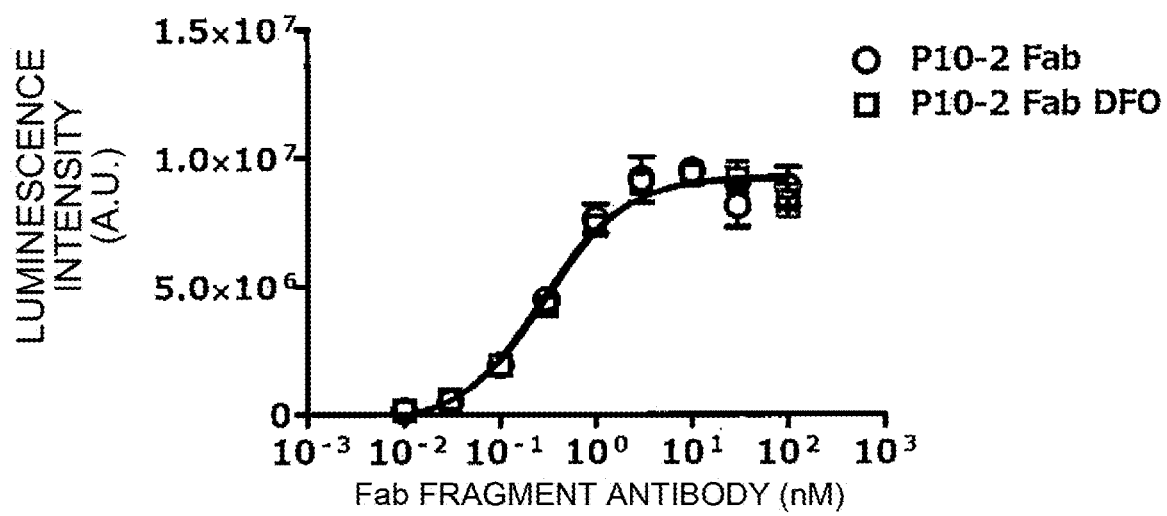
FIG. 3 is a graph and a table showing the binding activity of P10-2 Fab DFO and P10-2 Fab against human cancer-specific MUC1.

Binding activity against human cancer-specific MUC1 was compared as to P10-2 Fab DFO labeled by the method mentioned above with P10-2 Fab by Cell ELISA. Specifically, T-47D cells expressing human cancer-specific MUC1 were inoculated at $0.75 \times 10^4$ cells to a 96-well ELISA plate coated with collagen I, and cultured overnight. Then, the cells were fixed in formalin, and P10-2 Fab DFO or P10-2 Fab described above was reacted therewith. Then, a HRP-labeled goat anti-human Igκ antibody (Southern Biotechnology Associates, Inc.) was reacted as a secondary antibody. ECL Prime Western Blotting Detection Reagent (GE Healthcare Japan Corp.) was added thereto for luminescence, and the degree of the luminescence was examined. As a result, as shown in FIG. 3, P10-2 Fab DFO and P10-2 Fab had equivalent binding activity. P10-2 Fab was confirmed to be free from the attenuation of the binding activity by labeling with a chelating agent.

Example 8: Reactivity of P10-2 in Human Bladder Cancer Tissue Sample

In order to study the reactivity of P10-2 Fab in human bladder cancer, the study was made by immunostaining using a human bladder cancer tissue array (US Biomax, Inc., BC1201 b). When P10-2 Fab is used as a primary antibody, an anti-human antibody used as a secondary antibody cross-reacts with human tissues. Therefore, mouse chimeric P10-2 IgG (antibody in which the VH domain and the VL domain of P10-2 Fab were fused with mouse IgG2a CH1 to CH3 domains and a mouse κ chain CL domain, respectively) was prepared and used as a primary antibody. The human bladder cancer tissue array sample was reacted with a 3% hydrogen peroxide solution for 5 minutes and then washed with phosphate-buffered saline of pH 7.4. Then, mouse chimeric P10-2 IgG (0.25 μg/mL) was reacted, and then, One-Step Polymer-HRP antibody (BioGenex) was reacted as a secondary antibody. Super Sensitive DAB (BioGenex) was added thereto for color development. The positive reaction of staining for cancer tissues was determined as ±: very mildly positive, +: positive, ++: moderately positive, and +++: highly positive, and one case whose cancer tissues were not clear was excluded. As a result, positive reaction was found in 57 out of 59 studied cases with 11 cases for ±, 24 cases for +, 17 cases for ++, and 5 cases for +++(positive rate: 97%).

Example 9: Labeling of Chelated Fab Fragment with $^{89}$Zr $^{89}$Zr used was dissolved in a 1 M aqueous oxalic acid solution and produced as $^{89}$Zr-Oxalate (Okayama University). 20 μL of $^{89}$Zr-Oxalate (21.4 MBq) was neutralized with 10 μL of a 2 M aqueous sodium carbonate solution. Then, 70 μL of a 5 mg/mL solution of gentisic acid dissolved in 250 mM aqueous sodium acetate solution was added thereto. Further, 200 μL of a 500 mM aqueous HEPES (4-(2-hydroxyethyl)-1-piperazineethanesulfonic acid) solution containing 0.1% polysorbate 80 and 20% glycerol was added thereto. To this solution containing $^{89}$Zr, 100 μL of 9.5 mg/mL P10-2 Fab DFO was added and reacted at room temperature for 30 minutes. The obtained reaction mixture was purified using Amicon Ultra 10K-0.5 mL centrifugal filter (Merck Millipore) and further filtered through a membrane filter (Millex-GV 0.22™ 13 mm; Merck Millipore) to obtain $^{89}$Zr-labeled P10-2 Fab DFO (16.1 MBq) of interest. This $^{89}$Zr-labeled P10-2 Fab DFO was designated as P10-2 Fab DFO $^{89}$Zr. The obtained P10-2 Fab DFO $^{89}$Zr solution was analyzed using high-performance liquid chromatography (20AD series; Shimadzu Corp.). The retention time (UV: 10.192 min) of P10-2 Fab DFO was compared with the retention time (UV: 10.178 min, RI: 10.515 min) of P10-2 Fab DFO $^{89}$Zr. The respective retention times were equivalent, confirming that P10-2 Fab DFO was labeled with $^{89}$Zr. The HPLC analysis was carried out under the following conditions: column: BioSep SEC s3000 300×7.8 mm (Phenomenex Inc.), column temperature: room temperature, UV detector wavelength: 280 nm, mobile phase: phosphate buffer solution (Gibco, 10010-023), flow rate: 1 mL/min.

Example 10: Labeling of Fab Fragment with IRDye700DX

IRDye700DX NHS Ester (LI-COR Bioscience, Inc.) was used to label P10-2 Fab with IRDye700DX.
Specifically, a P10-2 Fab solution adjusted to 1 mg/mL with phosphate-buffered saline (pH 7.4) was supplemented with a 1/10 amount of a 1 M dipotassium hydrogen phosphate solution (pH 9). IRDye700DX NHS Ester was added thereto at a final concentration of 154 μg/mL, and the resultant was stirred at room temperature for 2 hours. After reaction, IRDye700DX-labeled P10-2 Fab was purified by recovery through Amicon Ultra 10K-15 mL centrifugal filter (Merck Millipore). This IRDye700DX-labeled P10-2 Fab was designated as P10-2 Fab IR700.

Figure 4:
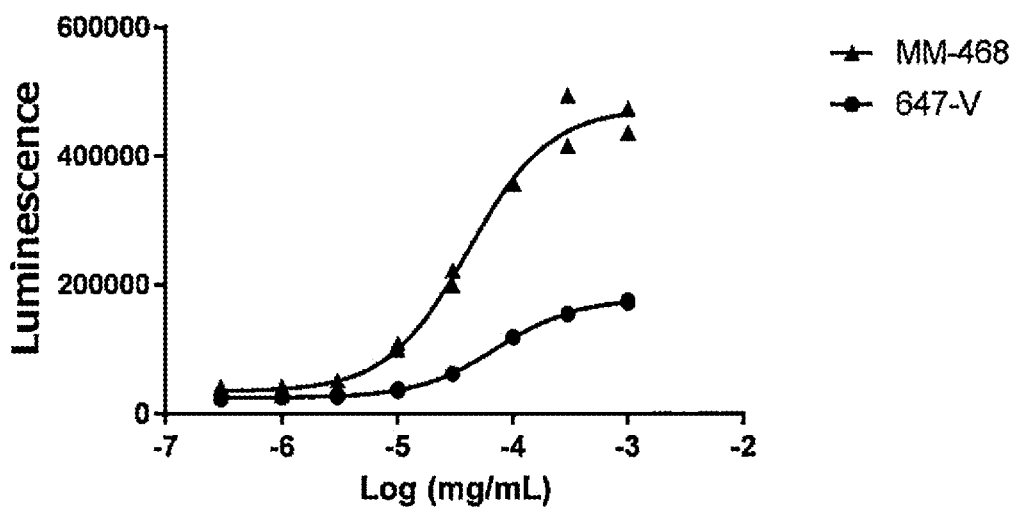
FIG. 4 is a graph showing the binding activity of P10-2 Fab against breast cancer cell line MDA-MB-468 cells (also referred to as MM-468 cells) and bladder cancer cell line 647-V cells expressing human cancer-specific MUC1. The horizontal axis depicts the concentration (Log(mg/mL)) of P10-2 Fab, and the vertical axis depicts luminescence.

Example 11: Binding Activity Evaluation of Fab Fragment Against Breast Cancer Cell Line and Bladder Cancer Cell Line The binding activity of P10-2 Fab in human breast cancer and bladder cancer was studied.
Specifically, human breast cancer cell line MDA-MB-468 cells (purchasable from ATCC; HTB-132; hereinafter, referred to as MM-468 cells) or human bladder cancer cell line 647-V cells (purchasable from DSMZ; ACC 414) expressing human cancer-specific MUC1 were inoculated at $1 \times 10^4$ cells per well to a 96-well ELISA plate and cultured overnight. Then, P10-2 Fab described above was reacted at a concentration of 0.0000003 to 0.001 mg/mL. Then, a horseradish peroxidase (HRP)-labeled goat anti-human IgG antibody (Medical & Biological Laboratories Co., Ltd.) was reacted as a secondary antibody. ECL Prime Western Blotting Detection Reagent (GE Healthcare Japan Corp.) was added thereto for luminescence, and the degree of the luminescence was examined. As a result, as shown in FIG. 4, P10-2 Fab was found to have binding activity against the human breast cancer cell line MM-468 cells and the human bladder cancer cell line 647-V cells.

Figure 5A:
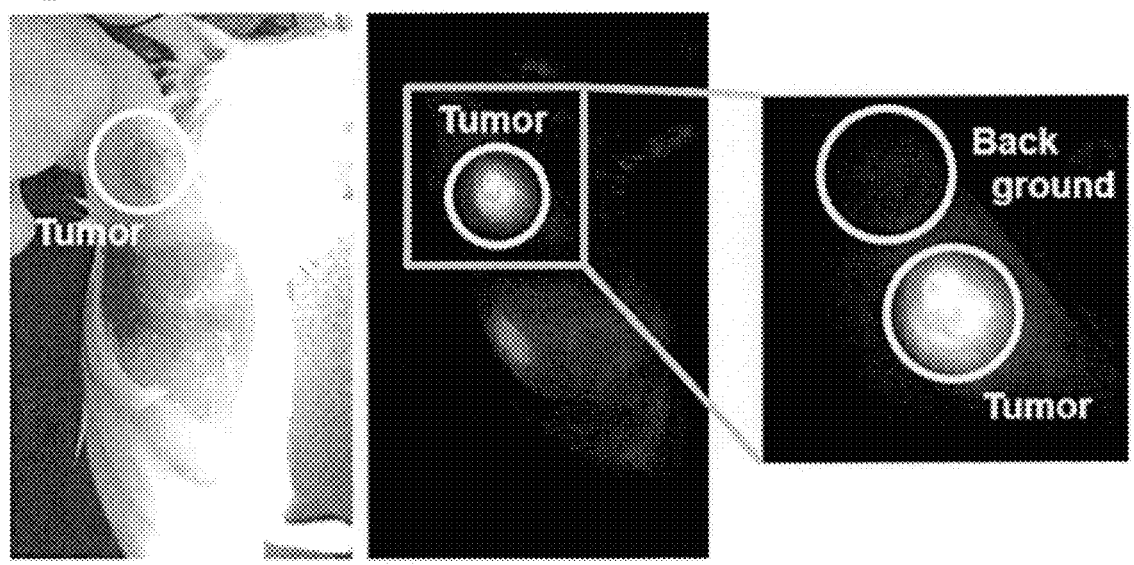
FIG. 5A is representative photographs taken with a usual camera (left) and a near-infrared fluorescence camera (center and right) 6 hours after administration of P10-2 Fab Dye which was intravenously administered at 3 mg/kg to subcutaneously cancer-bearing models.
Figure 5B:
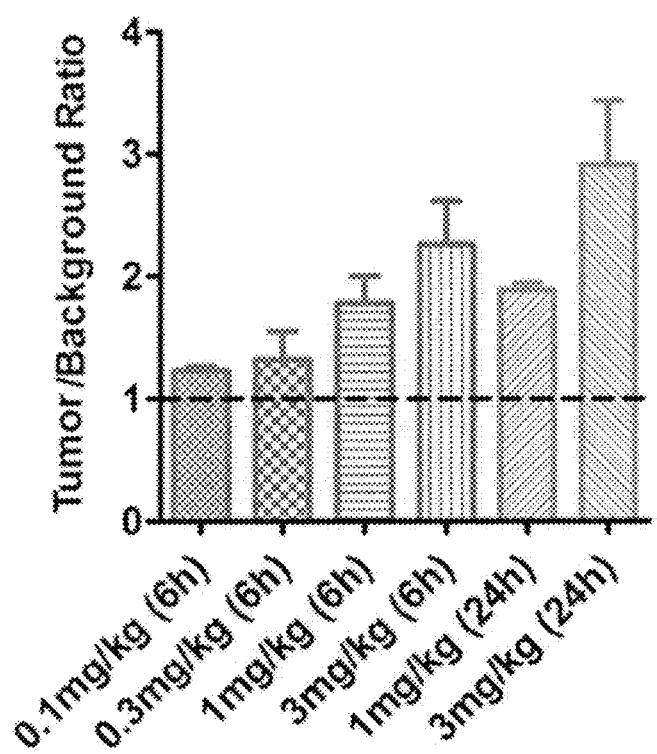
FIG. 5B is a graph quantifying the tumor/background ratio of a tumor site and a peritumoral background site and indicates mean+standard error. The horizontal axis depicts the dose and time after administration of P10-2 Fab Dye.

Example 12: Contrast Evaluation of Fluorescently Labeled Fab Fragment in Subcutaneously Cancer-Bearing Model $3 \times 10^6$ human breast cancer cell line MM-468 cells were subcutaneously transplanted as human cancer-specific MUC1-positive cells to the right back of each immunodeficient mouse (SCID mouse; Charles River Laboratories Japan, Inc.). Mice having tumorigenesis were selected approximately one month after the transplantation. P10-2 Fab Dye dissolved in phosphate-buffered saline (pH 7.4) was intravenously administered at a dose of 0.1, 0.3, 1 or 3 mg/kg (N=2 for the 0.1 mg/kg administration group, and N=3 for the 0.3, 1 and 3 mg/kg administration groups). Photographs were taken with a usual camera and a near-infrared fluorescence camera (Fluobeam (800 nm filter); Fluoptics) 6 hours and 24 hours after the P10-2 Fab Dye administration. The fluorescent brightness of a tumor site and a peritumoral background site in the image taken with the infrared fluorescence camera was measured. As a result, as shown in FIG. 5A, P10-2 Fab Dye was found to accumulate in the human cancer-specific MUC1-positive MM-468 tumor site and be clearly visible in the fluorescent image 6 hours after administration. As shown in FIG. 5B, the tumor/background ratio was found to elevate in a P10-2 Fab Dye dose-dependent manner in the range of 0.1 to 3 mg/kg. It was further obvious that the effect was sustained even 24 hours after administration. These results demonstrated that P10-2 Fab Dye permits detection of human MUC1-positive cancer cells from 6 hours to 24 hours after administration.

Figure 6:
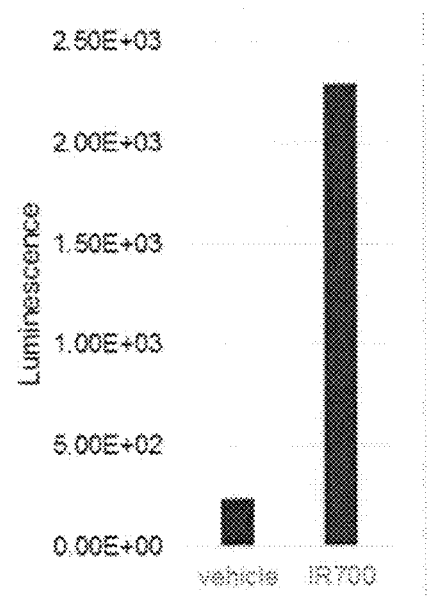
FIG. 6 is a graph quantifying luminescence of the tumor sites of administering P10-2 Fab IR700 to MM-468 cell-transplanted mice, euthanizing the animals 2 hours after the administration, excising tumor, taking photographs with IVIS SPECTRUM. The vertical axis depicts luminescence.

Example 13: Detection of Tumor with IRDye700DX Labeled Fab Fragment $5 \times 10^6$ MM-468 cells were subcutaneously transplanted to the right back of each immunodeficient mouse (nude mouse; Charles River Laboratories Japan, Inc.). This test was conducted at N=2. P10-2 Fab IR700 (3 mg/kg) or a vehicle (phosphate-buffered saline) was intravenously administered 40 days after the transplantation. The animals were euthanized 2 hours after the P10-2 Fab IR700 administration. Tumor was excised, and the luminescence of the tumor sites was measured by excitation at a wavelength of 675 nm and detection at a wavelength of 740 nm in IVIS SPECTRUM (PerkinElmer, Inc.). As a result, as shown in FIG. 6, P10-2 Fab IR700 was found to accumulate in MM-468 cells 2 hours after administration.

Example 14: Cytotoxicity Evaluation of IRDye700DX Labeled Fab Fragment

In order to study the utilization of P10-2 Fab IR700 in cancer treatment, cytotoxicity in photoimmunotherapy was evaluated.

Figure 7:
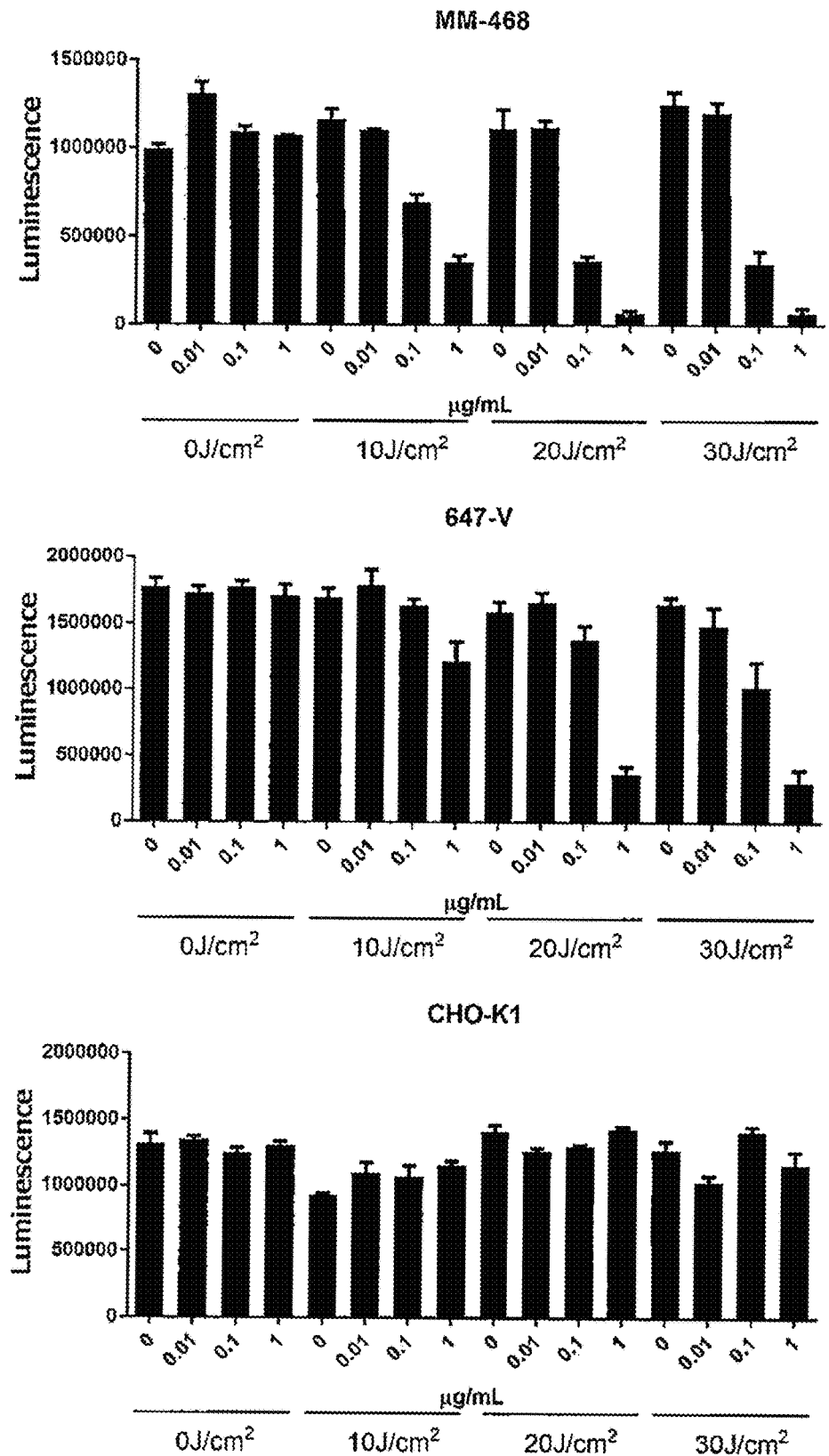
FIG. 7 is a graph showing results of measuring cytotoxicity of reacting P10-2 Fab IR700 to MM-468 cells, 647-V cells or CHO-K1 cells with irradiating light of Comparative Example. The upper column of the horizontal axis of each graph depicts the concentration of P10-2 Fab IR700, and the lower column depicts the exposure of light. The vertical axis depicts luminescence and indicates mean+standard error.

Specifically, human breast cancer cell line MM-468 cells, human bladder cancer cell line 647-V cells or CHO-K1 cells of Comparative Example (purchasable from ATCC; CCL-61) were inoculated at $5 \times 10^3$ cells per well to a 384-well white plate and cultured overnight. Then, P10-2 Fab IR700 was reacted at 0, 0.01, 0.1, or 1 µg/mL and then irradiated with 0 to 30 J/cm$^2$ of light having a wavelength of 680 nm. After the light irradiation, overnight culture was performed. CellTiter-Glo (Promega Corp.) was added thereto for luminescence, and the luminescence was measured to measure the number of live cells. This test was conducted using 3 wells under each condition. As a result, as shown in FIG. 7, it was obvious that P10-2 Fab IR700 exhibits cytotoxicity in a manner specific for the expression of human cancer-specific MUC1 by light irradiation.

Figure 8:
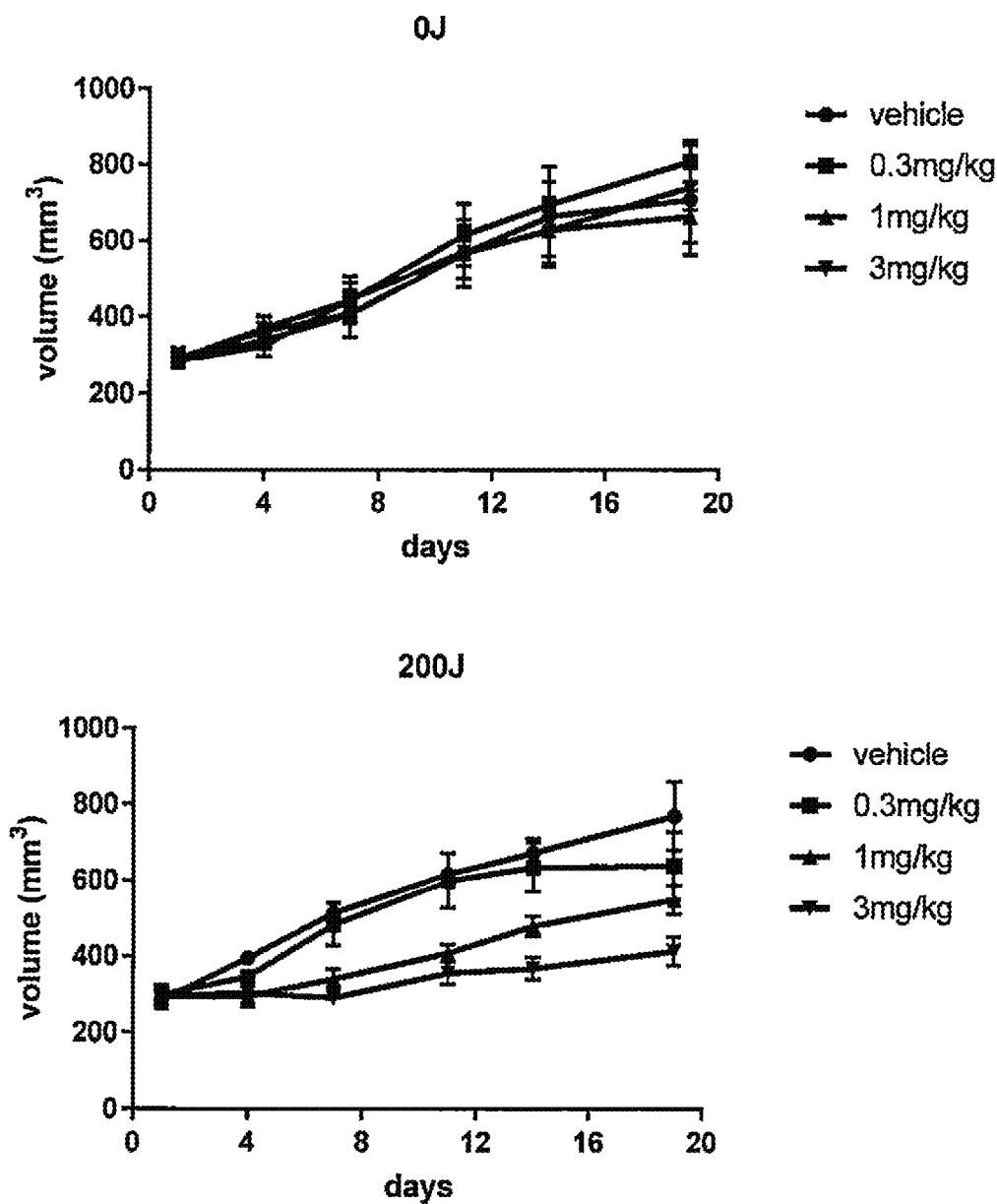
FIG. 8 is a graph showing results of measuring an antitumor effect depending on the presence or absence of light irradiation (0 J or 200 J) at the time of P10-2 Fab IR700 administration using MM-468 cell-transplanted nude mice. The horizontal axis depicts the number of days when the day on which tumor volume became 300 mm$^3$ was defined as day 1. The vertical axis depicts tumor volume (mm$^3$) and indicates mean+standard error.

Example 15: Antitumor Activity Evaluation of IRDye700DX Labeled Fab Fragment $5 \times 10^6$ MM-468 cells were subcutaneously transplanted to the right back of each immunodeficient mouse (nude mouse; Charles River Laboratories Japan, Inc.). This test was conducted at N=4. After tumor volume became 300 mm$^3$, P10-2 Fab IR700 (0.3, 1, or 3 mg/kg) was intravenously administered at days 1, 5, 8, 12 and 15. Phosphate-buffered saline was similarly administered to a vehicle group. On the day following the drug administration, irradiation with 0 or 200 J/cm$^2$ of light having a wavelength of 680 nm was performed, and the tumor volume was measured over time. As a result, as shown in FIG. 8, it was obvious that P10-2 Fab IR700 showed an antitumor effect in a manner dependent on a dose and light irradiation.

INDUSTRIAL APPLICABILITY

The anti-human MUC1 antibody Fab fragment of the present invention is expected to be useful in the diagnosis and/or treatment of cancers such as breast cancer, lung cancer, colorectal cancer, bladder cancer, skin cancer, thyroid gland cancer, stomach cancer, pancreatic cancer, kidney cancer, ovary cancer or uterine cervical cancer.

SEQUENCE LISTING FREE TEXT

SEQ ID NO: 1: Nucleotide sequence of DNA encoding a P10-1 Fab heavy chain fragment
SEQ ID NO: 2: Amino acid sequence of the P10-1 Fab heavy chain fragment
SEQ ID NO: 3: Nucleotide sequence of DNA encoding a P10-2 Fab heavy chain fragment
SEQ ID NO: 4: Amino acid sequence of the P10-2 Fab heavy chain fragment
SEQ ID NO: 5: Nucleotide sequence of DNA encoding an antibody light chain
SEQ ID NO: 6: Amino acid sequence of the antibody light chain
SEQ ID NO: 7: Nucleotide sequence of DNA encoding a P10-1 Fab heavy chain variable region
SEQ ID NO: 8: Amino acid sequence of the P10-1 Fab heavy chain variable region
SEQ ID NO: 9: Nucleotide sequence of DNA encoding a P10-2 Fab heavy chain variable region
SEQ ID NO: 10: Amino acid sequence of the P10-2 Fab heavy chain variable region
SEQ ID NO: 11: Nucleotide sequence of DNA encoding an antibody light chain variable region
SEQ ID NO: 12: Amino acid sequence of the antibody light chain variable region
SEQ ID NO: 13: Heavy chain signal sequence
SEQ ID NO: 14: Light chain signal sequence
SEQ ID NO: 15: Tandem repeat sequence of the extracellular domain of MUC1

What is claimed is:

1. A conjugate comprising one or more labeling moiety and an anti-human MUC1 antibody Fab fragment, wherein the labeling moiety is (i) a fluorescent dye and a linker or (ii) a fluorescent dye, and wherein the anti-human MUC1 antibody Fab fragment is selected from the group consisting of the following (a) and (b):
   (a) an anti-human MUC I antibody Fab fragment comprising a heavy chain fragment comprising a heavy chain variable region consisting of the amino acid sequence represented by SEQ ID NO: 8 or SEQ ID NO: 10 and a light chain comprising a light chain variable region consisting of the amino acid sequence represented by SEQ ID NO: 12; and
   (b) an anti-human MUC1 antibody Fab fragment comprising a heavy chain fragment comprising a heavy chain variable region derived from a heavy chain variable region consisting of the amino acid sequence represented by SEQ ID NO: 8 or SEQ ID NO: 10 by the modification of glutamine at amino acid position 1 of SEQ ID NO: 8 or SEQ ID NO: 10 into pyroglutamic acid, and a light chain comprising a light chain variable region consisting of the amino acid sequence represented by SEQ ID NO: 12.

2. The conjugate according to claim 1 wherein the anti-human MUC1 antibody Fab fragment is selected from the group consisting of the following (a) and (b):
   (a) an anti-human MUC1 antibody Fab fragment comprising a heavy chain fragment consisting of the amino acid sequence represented by SEQ ID NO: 2 or SEQ ID NO: 4 and a light chain consisting of the amino acid sequence represented by SEQ ID NO: 6; and
   (b) an anti-human MUC1 antibody Fab fragment comprising a heavy chain fragment derived from a heavy chain fragment consisting of the amino acid sequence represented by SEQ ID NO: 2 or SEQ ID NO: 4 by the modification of glutamine at amino acid position 1 of SEQ ID NO: 2 or SEQ ID NO: 4 into pyroglutamic acid, and a light chain consisting of the amino acid sequence represented by SEQ ID NO: 6.

3. The conjugate according to claim 1 wherein the anti-human MUC1 antibody Fab fragment is selected from the group consisting of the following (a) and (b):
   (a) an anti-human MUC1 antibody Fab fragment comprising a heavy chain fragment comprising a heavy chain variable region consisting of the amino acid sequence represented by SEQ ID NO: 10 and a light chain comprising a light chain variable region consisting of the amino acid sequence represented by SEQ ID NO: 12; and
   (b) an anti-human MUC1 antibody Fab fragment comprising a heavy chain fragment comprising a heavy chain variable region derived from a heavy chain variable region consisting of the amino acid sequence represented by SEQ ID NO: 10 by the modification of glutamine at amino acid position 1 of SEQ ID NO: 10 into pyroglutamic acid, and a light chain comprising a light chain variable region consisting of the amino acid sequence represented by SEQ ID NO: 12.

4. The conjugate according to claim 3 wherein the anti-human MUC1 antibody Fab fragment is selected from the group consisting of the following (a) and (b):
   (a) an anti-human MUC1 antibody Fab fragment comprising a heavy chain fragment consisting of the amino acid sequence represented by SEQ ID NO: 4 and a light chain consisting of the amino acid sequence represented by SEQ ID NO: 6; and
   (b) an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

5. The conjugate according to claim 4 wherein the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6.

6. The conjugate according to claim 4 wherein the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6.

7. The conjugate according to claim 1, wherein the fluorescent dye is a fluorescent dye selected from the group consisting of the following formula (B) and the following formula (C):

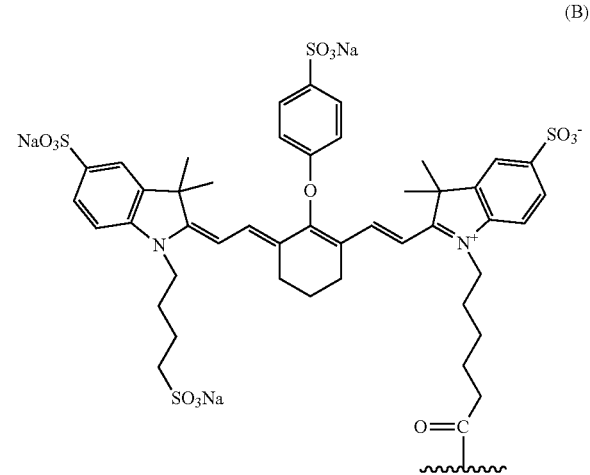

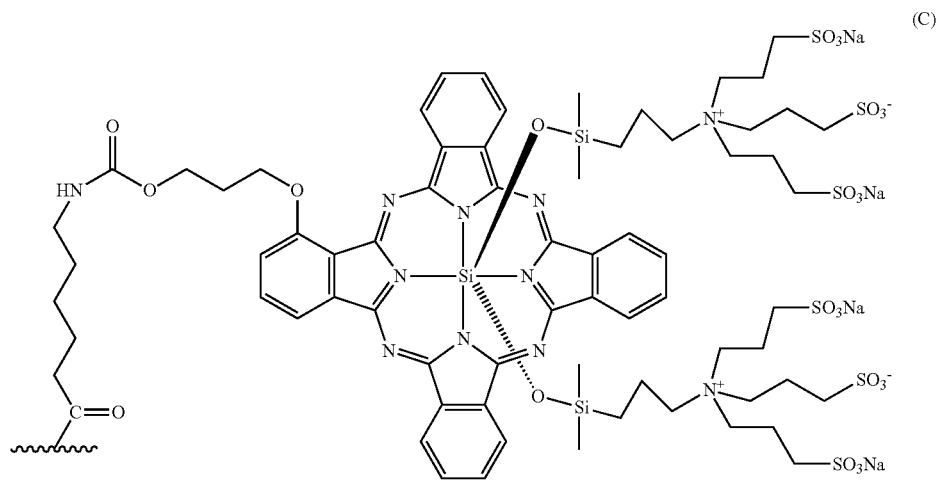

wherein the wavy line represents binding to the anti-human MUC1 antibody Fab fragment or the linker.

8. The conjugate according to claim 7, wherein the wavy line represents binding to the anti-human MUC1 antibody Fab fragment, and the anti-human MUC1 antibody Fab fragment is bound via an amino group thereof to the carbon atom of a labeling moiety terminal C(=O) group.

9. The conjugate according to claim 8, wherein the labeling moiety is a fluorescent dye represented by formula (B).

10. A conjugate selected from the group consisting of the following (a) to (c):
(a) the conjugate according to claim 9 wherein the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6;
(b) the conjugate according to claim 9 wherein the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6; and
(c) a conjugate which is a mixture of (a) and (b).

11. The conjugate according to claim 8, wherein the labeling moiety is a fluorescent dye represented by formula (C).

12. A conjugate selected from the group consisting of the following (a) to (c):
(a) the conjugate according to claim 11 wherein the anti-human MUC1 antibody Fab fragment is an anti-human MUC1 antibody Fab fragment comprising a heavy chain fragment consisting of the amino acid sequence represented by SEQ ID NO: 4 and a light chain consisting of the amino acid sequence represented by SEQ ID NO: 6;
(b) the conjugate according to claim 11 wherein the anti-human MUC1 antibody Fab fragment is an anti-human MUC1 antibody Fab fragment comprising a heavy chain fragment derived from a heavy chain fragment consisting of the amino acid sequence represented by SEQ ID NO: 4 by the modification of glutamine at amino acid position 1 of SEQ ID NO: 4 into pyroglutamic acid, and a light chain consisting of the amino acid sequence represented by SEQ ID NO: 6; and
(c) a conjugate which is a mixture of (a) and (b).

13. A composition comprising the conjugate according to claim 1, and a pharmaceutically acceptable carrier.

14. A composition comprising the conjugate according to claim 10 and a pharmaceutically acceptable carrier.

15. A composition comprising the conjugate according to claim 12 and a pharmaceutically acceptable carrier.

16. A method for diagnosing breast cancer or bladder cancer, comprising preoperatively or intraoperatively administering the conjugate according to claim 1 to a subject in need thereof.

17. A method for treating breast cancer or bladder cancer, comprising administering a therapeutically effective amount of the conjugate according to claim 1 to a subject in need thereof.

* * * * *

SEQUENCE LISTING

<160> NUMBER OF SEQ ID NOS: 15

<210> SEQ ID NO 1
<211> LENGTH: 669

```
<212> TYPE: DNA
<213> ORGANISM: Artificial Sequence
<220> FEATURE:
<223> OTHER INFORMATION: DNA encoding P10-1 Fab heavy chain fragment

<400> SEQUENCE: 1
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccaccctg gcagcggcat catctaccac     180
aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgccta ttggggacag ggcacccctcg tgaccgtgtc ctcagcctcc     360
accaagggcc catcggtctt cccccctggca ccctcctcca gagcacctc tgggggcaca     420 gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctta gtagcgtggt gaccgtgccc tccagcagct gggcaccca gacctacatc     600 tgcaacgtga atcacaagcc cagcaacacc aaggtggaca agaaagttga gcccaaatct     660
tgtgactga                                                             669

<210> SEQ ID NO 2
<211> LENGTH: 222
<212> TYPE: PRT
<213> ORGANISM: Artificial Sequence
<220> FEATURE:
<223> OTHER INFORMATION: P10-1 Fab heavy chain fragment

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Ala Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp
            210                 215                 220

<210> SEQ ID NO 3
<211> LENGTH: 669
<212> TYPE: DNA
<213> ORGANISM: Artificial Sequence
<220> FEATURE:
<223> OTHER INFORMATION: DNA encoding P10-2 Fab heavy chain fragment

<400> SEQUENCE: 3
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccaccctg gcagcggcat catctaccac     180
aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgacta ttggggacag ggcaccctcg tgaccgtgtc ctcagcctcc     360
accaagggcc catcggtctt ccccctggca ccctcctcca agagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctta gtagcgtggt gaccgtgccc tccagcagct tgggcaccca gacctacatc     600
tgcaacgtga atcacaagcc cagcaacacc aaggtggaca agaaagttga gcccaaatct     660
tgtgactga                                                             669

<210> SEQ ID NO 4
<211> LENGTH: 222
<212> TYPE: PRT
<213> ORGANISM: Artificial Sequence
<220> FEATURE:
<223> OTHER INFORMATION: P10-2 Fab heavy chain fragment

<400> SEQUENCE: 4

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln

```
                        165                 170                 175
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp
    210                 215                 220

<210> SEQ ID NO 5
<211> LENGTH: 660
<212> TYPE: DNA
<213> ORGANISM: Artificial Sequence
<220> FEATURE:
<223> OTHER INFORMATION: DNA encoding antibody light chain

<400> SEQUENCE: 5
gacgtcgtga tgacccagac ccctctgagc ctgagcgtga cacctggaca gcctgccagc      60
atcagctgca gatccagcca gagcatcgtg cacagcaacg gcaacaccta cctggaatgg     120
tatctgcaga gcccggccag agcccccag ctgctgatct acagggtgtc caaccggttc     180
agcggcgtgc ccgacagatt ttctggcagc ggctccggca ccgacttcac cctgaagatc     240 tcccggggtgg aagccgagga cgtgggcgtg tactactgtt tcaaggcag ccacggcccc     300 tggacctttg gccagggaac aaagctggaa atcaagcgta cggtggctgc accatctgtc     360
ttcatcttcc cgccatctga tgagcagttg aaatctggaa ctgcctctgt tgtgtgcctg     420
ctgaataact tctatcccag agaggccaaa gtacagtgga aggtggataa cgccctccaa     480
tcgggtaact cccaggagag tgtcacagag caggacagca aggacagcac ctacagcctg     540
agcagcaccc tgacgctgag caaagcagac tacgagaaac acaaagtcta cgcctgcgaa     600
gtcacccatc agggcctgag ctcgcccgtc acaaagagct tcaacagggg agagtgttag     660

<210> SEQ ID NO 6
<211> LENGTH: 219
<212> TYPE: PRT
<213> ORGANISM: Artificial Sequence
<220> FEATURE:
<223> OTHER INFORMATION: Antibody light chain

<400> SEQUENCE: 6

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Gly Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140
```

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 354
<212> TYPE: DNA
<213> ORGANISM: Artificial Sequence
<220> FEATURE:
<223> OTHER INFORMATION: DNA encoding P10-1 Fab heavy chain variable
      region

<400> SEQUENCE: 7
caggtgcagc tggtgcagtc tggcgccgaa gtgaagaaac caggcgccag cgtgaaggtg      60
tcctgcaagg ccagcggcta caccttcacc aactacggcc tgagctgggt gcgccaggct     120
cctggacagg gactggaatg gatgggcgag aaccacccctg cagcggcat catctaccac     180 aacgagaagt tccggggcag agtgaccctg accgccgacc ggagcaccag caccgcctac     240
atggaactga gcagcctgcg gagcgaggac accgccgtgt actactgtgc cagaagcagc     300
ggcaccagag gctttgccta ttggggacag ggcacccctcg tgaccgtgtc ctca          354

<210> SEQ ID NO 8
<211> LENGTH: 118
<212> TYPE: PRT
<213> ORGANISM: Artificial Sequence
<220> FEATURE:
<223> OTHER INFORMATION: P10-1 Fab heavy chain variable region

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Ser Gly Thr Arg Gly Phe Ala Tyr Trp Gly Gln Gly Thr
            100                 105                 110

Leu Val Thr Val Ser Ser
        115

<210> SEQ ID NO 9
<211> LENGTH: 354
<212> TYPE: DNA
<213> ORGANISM: Artificial Sequence
<220> FEATURE:

<223> OTHER INFORMATION: DNA encoding P10-2 Fab heavy chain variable
      region

<400> SEQUENCE: 9
caggtgcagc tggtgcagtc tggcgccgaa gtgaagaaac caggcgccag cgtgaaggtg    60
tcctgcaagg ccagcggcta caccttcacc aactacggcc tgagctgggt gcgccaggct   120
cctggacagg gactggaatg gatgggcgag aaccaccctg gcagcggcat catctaccac   180
aacgagaagt tccggggcag agtgaccctg accgccgacc ggagcaccag caccgcctac   240
atggaactga gcagcctgcg gagcgaggac accgccgtgt actactgtgc cagaagcagc   300
ggcaccagag ctttgactat tggggacag ggcaccctcg tgaccgtgtc ctca          354

<210> SEQ ID NO 10
<211> LENGTH: 118
<212> TYPE: PRT
<213> ORGANISM: Artificial Sequence
<220> FEATURE:
<223> OTHER INFORMATION: P10-2 Fab heavy chain variable region

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Glu Asn His Pro Gly Ser Gly Ile Ile Tyr His Asn Glu Lys Phe
    50                  55                  60

Arg Gly Arg Val Thr Leu Thr Ala Asp Arg Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Gly Thr Arg Gly Phe Asp Tyr Trp Gly Gln Gly Thr
            100                 105                 110

Leu Val Thr Val Ser Ser
        115

<210> SEQ ID NO 11
<211> LENGTH: 339
<212> TYPE: DNA
<213> ORGANISM: Artificial Sequence
<220> FEATURE:
<223> OTHER INFORMATION: DNA encoding antibody light chain variable
      region

<400> SEQUENCE: 11
gacgtcgtga tgacccagac ccctctgagc ctgagcgtga cacctggaca gcctgccagc    60
atcagctgca gatccagcca gagcatcgtg cacagcaacg gcaacaccta cctggaatgg   120
tatctgcaga gcccggcca gagccccag ctgctgatct acagggtgtc caaccggttc     180
agcggcgtgc ccgacagatt ttctggcagc ggctccggca ccgacttcac cctgaagatc   240
tcccgggtgg aagccgagga cgtgggcgtg tactactgtt ttcaaggcag ccacggcccc   300 tggaccttttg ccagggaac aaagctggaa atcaagcgt                         339

<210> SEQ ID NO 12
<211> LENGTH: 113
<212> TYPE: PRT
<213> ORGANISM: Artificial Sequence

```
<220> FEATURE:
<223> OTHER INFORMATION: Antibody light chain variable region

<400> SEQUENCE: 12

Asp Val Val Met Thr Gln Thr Pro Leu Ser Leu Ser Val Thr Pro Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Arg Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Gly Pro Trp Thr Phe Gly Gln Gly Thr Lys Leu Glu Ile Lys
            100                 105                 110

Arg

<210> SEQ ID NO 13
<211> LENGTH: 19
<212> TYPE: PRT
<213> ORGANISM: Artificial Sequence
<220> FEATURE:
<223> OTHER INFORMATION: Heavy chain signal sequence

<400> SEQUENCE: 13

Met Glu Trp Ser Trp Val Phe Leu Phe Phe Leu Ser Val Thr Thr Gly
1               5                   10                  15

Val His Ser

<210> SEQ ID NO 14
<211> LENGTH: 20
<212> TYPE: PRT
<213> ORGANISM: Artificial Sequence
<220> FEATURE:
<223> OTHER INFORMATION: Light chain signal sequence

<400> SEQUENCE: 14

Met Ser Val Pro Thr Gln Val Leu Gly Leu Leu Leu Leu Trp Leu Thr
1               5                   10                  15

Asp Ala Arg Cys
            20

<210> SEQ ID NO 15
<211> LENGTH: 20
<212> TYPE: PRT
<213> ORGANISM: Artificial Sequence
<220> FEATURE:
<223> OTHER INFORMATION: Tandem repeat sequence of an extracellular
      domain of MUC1

<400> SEQUENCE: 15

His Gly Val Thr Ser Ala Pro Asp Thr Arg Pro Ala Pro Gly Ser Thr
1               5                   10                  15

Ala Pro Pro Ala
            20
```